US010596166B2

(12) United States Patent
Callizot

(10) Patent No.: US 10,596,166 B2
(45) Date of Patent: Mar. 24, 2020

(54) COMBINATION COMPOSITION COMPRISING HUPERZINE

(71) Applicant: NEURO-SYS, Gardanne (FR)

(72) Inventor: Noelle Callizot, Rognonas (FR)

(73) Assignee: NEURALIA, Gardanne (FR)

( * ) Notice: Subject to any disclaimer, the term of this patent is extended or adjusted under 35 U.S.C. 154(b) by 0 days.

(21) Appl. No.: 15/735,984

(22) PCT Filed: Jun. 15, 2016

(86) PCT No.: PCT/EP2016/000997
§ 371 (c)(1),
(2) Date: Dec. 13, 2017

(87) PCT Pub. No.: WO2016/202453
PCT Pub. Date: Dec. 22, 2016

(65) Prior Publication Data
US 2018/0169089 A1 Jun. 21, 2018

(30) Foreign Application Priority Data
Jun. 15, 2015 (EP) ..................................... 15305930

(51) Int. Cl.
*A61K 31/4748* (2006.01)
*A61K 31/192* (2006.01)
*A61K 36/11* (2006.01)
*A61P 25/28* (2006.01)
*A61K 36/00* (2006.01)

(52) U.S. Cl.
CPC ........ *A61K 31/4748* (2013.01); *A61K 31/192* (2013.01); *A61K 36/00* (2013.01); *A61K 36/11* (2013.01); *A61P 25/28* (2018.01)

(58) Field of Classification Search
CPC .............. A61K 2300/00; A61K 31/192; A61K 31/4748; A61K 36/11; A61K 36/00; A61P 25/28
See application file for complete search history.

(56) References Cited

U.S. PATENT DOCUMENTS

| 2006/0216251 A1* | 9/2006 | Morariu | A61K 8/41 424/59 |
| 2007/0065396 A1* | 3/2007 | Morariu | A61K 8/44 424/74 |
| 2007/0286911 A1* | 12/2007 | Xie | A61K 31/435 424/725 |

FOREIGN PATENT DOCUMENTS

| CA | 240152 A | 5/1924 |
| EP | 2 343 065 A1 | 7/2011 |
| WO | 2008/108825 A2 | 9/2008 |
| WO | 2011/132157 A1 | 10/2011 |

OTHER PUBLICATIONS

Huang et al (Journal UOEH, 2016, vol. 38, pp. 139-148) (Year: 2016).*
Rasoanaivo et al (Malaria Journal, 2011, vol. 10, pp. 1-12) (Year: 2011).*
Adlard, P. A., et al., "Morphologically Distinct Plaque Types Differently Affect Dendritic Structure and Organisation in the Early and Late Stages of Alzheimer's Disease," Acta Neuropathol, vol. 103, 2002, pp. 377-383.
Anwar, J., et al., "Effects of Caffeic Acid on Behavioral Parameters and on the Activity of Acetylcholinesterase in Different Tissues from Adult Rats," Pharmacology, Biochemistry and Behavior, vol. 103, 2012, pp. 386-394.
Badia, A., et al., "Synthesis and Evaluation of Tacrine-Huperzine A Hybrids as Acetylcholinesterase Inhibitors of Potential Interest for the Treatment of Alzheimer's Disease," Bioorganic & Medicinal Chemistry, vol. 6, 1998, pp. 427-440.
Braun, S., et al., "Neurotrophins Increase Motoneurons' Ability to Innervate Skeletal Muscle Fibers in Rat Spinal Cord-Human Muscle Cocultures," Journal of the Neurological Sciences, vol. 136, 1996, pp. 17-23.
Callizot, N., et al., "Operational Dissection of β-Amyloid Cytopathic Effects on Cultured Neurons," Journal of Neuroscience Research, vol. 91, 2013, pp. 706-716.
Campos-Peña, et al., "Alzheimer Disease: The Role of Aβ in the Glutamatergic System," Neurochemistry, 2014, pp. 286-315.
Combes, M., et al., "Glutamate Protects Neuromuscular Junctions from Deleterious Effects of β-Amyloid Peptide and Conversely an In Vitro Study in a Nerve-Muscle Coculture," Journal of Neuroscience Research, vol. 93, 2015, pp. 633-643.
Esiri, M., et al., "Prevalence of Alzheimer Plaques in AIDS," J. Neurol Neurosurg Psychiatry, vol. 65, 1998, pp. 29-33.
Hsia, A., et al., "Plaque-Independent Disruption of Neural Circuits in Alzheimer's Disease Mouse Models," Proc. Natl. Acad. Sci., vol. 96, 1999, pp. 3228-3233.
Jeong, C., et al., "Neuroprotective and Anti-Oxidant Effects of Caffeic Acid Isolated from Erigeron Annuus Leaf," Chinese Medicine, vol. 6, 2011, pp. 1-9.
Li, W., et al., "Determination of Huperzine A in Human Plasma by Liquid Chromatography-Electrospray Tandem Mass Spectrometry: Application to a Bioequivalence Study on Chinese Volunteers," Biomedical Chromatography, vol. 22, 2008, pp. 354-360.
Chen, L., et al., "Chinese Herbs and Herbal Extracts for Neuroprotection of Dopaminergic Neurons and Potential Therapeutic Treatment of Parkinson's Disease," CNS & Neurological Disorders—Drug Targets, vol. 6, 2007, pp. 273-281.
Meraz-Rios, M., et al., "Early Onset Alzheimer's Disease and Oxidative Stress," Oxidative Medicine and Cellular Longevity, vol. 2014, 2014, pp. 1-14.

(Continued)

*Primary Examiner* — Mark V Stevens
(74) *Attorney, Agent, or Firm* — Young & Thompson

(57) ABSTRACT

A combination composition including as active components, in synergistically effective amounts a huperzine of natural or synthetic origin, a pharmaceutically acceptable salt thereof or a plant extract containing huperzine, and at least two compounds selected from the group consisting of: hydroxycinnamic acids, anthoxanthins, anthocyanins and mixtures thereof.

14 Claims, 40 Drawing Sheets

(56) References Cited

OTHER PUBLICATIONS

Sakono, M, et al., "Amyloid Oligomers: Formation and Toxicity of Aβ Oligomers," The FEBS Journal, 2010, pp. 1348-1358.

Schinelli, S., et al., "1-Mthyl-4-Phenyl-1,2,3,6-Tetrahydropyridine Metabolism and 1-Methyl-4-Phenylpyridinium Uptake in Dissociated Cell Cultures from the Embryonic Mesencephalon," Journal of Neurochemistry, vol. 50, No. 6, 1998, pp. 1900-1907.

Shi, Y., et al., "Novel 16-Substituted Bifunctional Derivatives of Huperzine B: Multifunctional Cholinesterase Inhibitors," Acta Pharmacologica Sinica, vol. 30, 2009, pp. 1195-1203.

Singer, C., et al., "The Mitogen-Activated Protein Kinase Pathway Mediates Estrogen Neuroprotection After Glutamate Toxicity in Primary Cortical Neurons," The Journal of Neuroscience, vol. 19, No. 7, 1999, pp. 2455-2463.

Yuan-Ming, et al., "Determination of Hupzine A in Huperzia Serrata by HPLC," Chinese Traditional and Herbal Drugs, vol. 33, No. 12, 2002, pp. 1078-1080; with partial English translation.

Visanji, N., et al., "PYM50028, A Novel, Orally Active, Nonpeptide Neurotrophic Factor Inducer, Prevents and Reverses Neuronal Damage Induced by MPP+ in Mesencephalic Neurons and by MPTP in a Mouse Model of Parkinson's Disease," The FASEB Journal, vol. 22, No. 7, 2008, pp. 2488-2497.

Wang, B., et al., "Efficacy and Safety of Natural Acetylcholinesterase Inhibitor Huperzine A in the Treatment of Alzheimer's Disease: An Updated Meta-Analysis," J. Neural Transm, vol. 116, 2009, pp. 457-465.

Xing, S., et al., "Huperzine A in the Treatment of Alzheimer's Disease and Vascular Dementia: A Meta-Analysis," Evidence-Based Complementary and Alternative Medicine, vol. 2014, 2013, pp. 1-10.

Xu, S. et al., "Huperzine-A in Capsules and Tablets for Treating Patients with Alzheimer Disease," Acta Pharmacol. Sin., vol. 20, 1999, pp. 486-490.

Yang, G., et al., "Huperzine A for Alzherimer's Disease: A Systematic Review and Meta-Analysis of Randomized Clinical Trials," PLOS One, vol. 8, Issue 9, 2013, pp. 1-8.

Zhu, X., et al., "Improvement of Impaired Memory in Mice by Huperzine A and Huperzine B," Acta Pharmacologica Sinica, vol. 9, No. 6, 1988, pp. 492-497; with partial English translation.

Wang, Y., "Retrospect and Prospect of Active Principles from Chinese Herbs in the Treatment of Dementia," Acta Pharmacologica Sinica, vol. 31, No. 6, 2010, pp. 649-664.

Yan, J., et al., "Protection Against β-Amyloid Peptide Toxicity In Vivo with Long-Term Administration of Ferulic Acid," British Journal of Pharmacology, vol. 133, 2001, pp. 89-96.

Kahn, K., et al., "Impact of Caffeic Acid on Aluminium Chloride-Induced Dementia in Rats," Journal of Pharmacy and Pharmacology, vol. 65, No. 12, 2013, pp. 1745-1752.

Gutierres, J., et al., "Neuroprotective Effect of Anthocyanins on Acetylcholinesterase Activity and Attenuation of Scopolamine-Induced Amnesia in Rats," International Journal of Developmental Neuroscience, vol. 33, 2014, pp. 88-97.

International Search Report issued in Application No. PCT/EP2016/000997, dated Sep. 28, 2016.

Nakamura, S., et al., "The Effect of Ferulic Acid and Garden Angelica Root Extract Preparation ANM 176 (TM) on Cognitive Function of Alzheimer's Disease Patients," Geriatric Medicine, vol. 46, No. 12, 2008, 1511-1519; with computer-generated English translation.

* cited by examiner

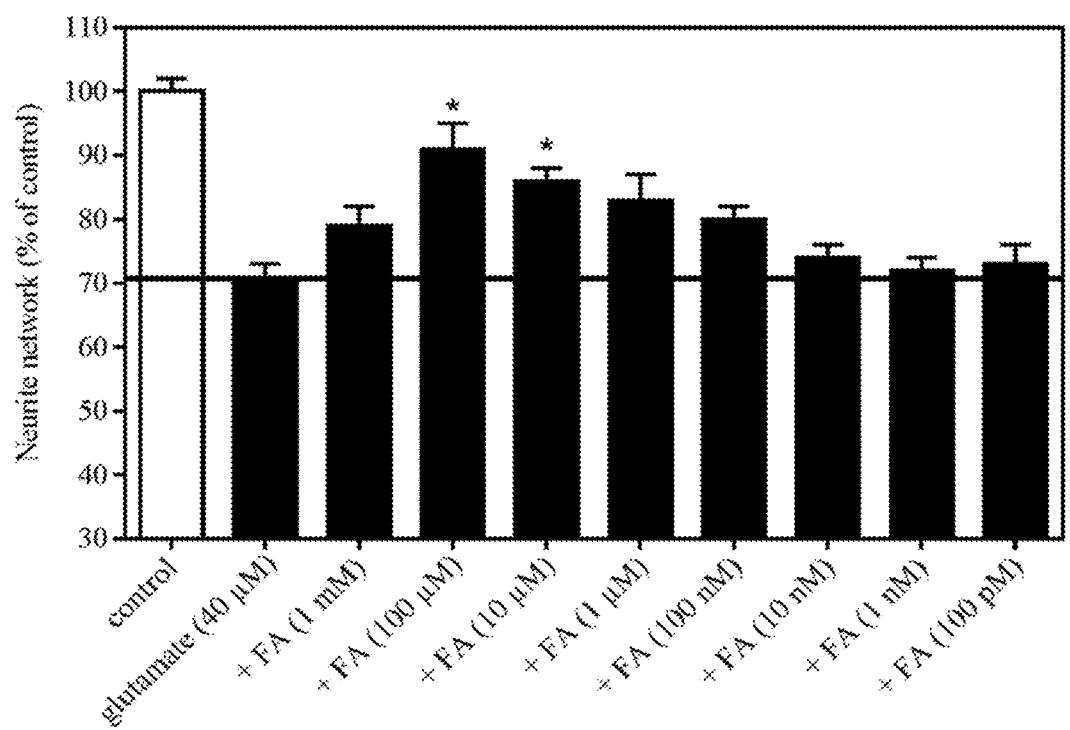

COMBINATION COMPOSITION COMPRISING HUPERZINE

FIELD OF THE INVENTION

The present invention relates generally to a composition comprising huperzine, the preparation methods and usage thereof for treating neurodegenerative diseases. The invention relates more specifically to a combination composition for use in preventing or treating neurodegenerative decline and dysfunction in a subject suffering from a neurodegenerative disease or condition, especially Alzheimer's disease.

BACKGROUND

Alzheimer's disease (AD) is a major public health problem due to its increasing prevalence, long duration, caregiver burden and high financial cost of care. In Alzheimer's disease, the most characteristic neuropathological changes are the formation of neurofibrillary tangles and neuritic plaques characterized by the presence of bundles of paired helical filaments that accumulate in the degenerating neurites and neuronal cell bodies. Classic neuritic plaques have a central dense core of β-amyloid peptide surrounded by a corona of dystrophic neurites (Esiri M M et al., J Neurol Neurosurg Psychiatry (1998) 65:29-33). Although the protein composition of the paired helical filaments is ill-defined, a number of microtubule-associated proteins have been implicated in these lesions. So, it has been reported that in the brains affected by Alzheimer's disease, the levels of microtubule-associated protein 2 (MAP 2) are usually decreased [Adlard P A, Vickers J C; Acta Neuropathol (2002) 103: 377-383; Hsia A Y et al.; Proc Natl Acad Sci USA (1999) 96: 3228-3233].

Currently there is no treatment for Alzheimer's disease. Current efforts to develop an effective treatment for AD are based upon the finding that Alzheimer's disease patients suffer from marked deficits in cholinergic neurotransmitter system, resulting in a deficiency in acetylcholine concentration in the central nervous system. Treatment approaches include precursors for acetylcholine synthesis, cholinergic agonists, acetylcholine release enhancers and acetylcholinesterase (AChE) inhibitors. To date, the most effective approach has been the use of AChE-inhibitors, such as tacrine, donepezil, and rivastigmine.

Previous studies showed that AD pathogenesis is triggered by the accumulation and deposition of toxic β-amyloid peptide (Aβ) in the central nervous system [Callizot et al., J. Neurosc. Res. (2013) 91(5):706-16]. Herbal medications targeting the mechanisms underlying Aβ-accumulation might be an effective approach to preventing the disease. Parkinson's disease (PD) is the second most common neurodegenerative disorder in the United States. The predominant motor symptoms of PD including slow movement, resting tremor, rigidity and gait disturbance are caused by the loss of dopaminergic neurons in the substantia nigra (SN). Epidemiological studies suggest that the use of pesticides increases the risk of PD, possibly via reduced activity of complex I in the mitochondrial respiratory chain in the substantia nigra and result in the pathogenesis of PD. 1-methyl-4-phenyl-1,2,3,6-tetrahydropyridine (MPTP) and its derivative form (MPP$^+$), a mitochondrial complex I inhibitor, has been widely used to produce toxin models of sporadic PD. This toxin is used to mimic in vitro PD [Visanji. et al., FASEB J. 2008; 22(7):2488-97].

Amyotrophic lateral sclerosis (ALS), also called Lou Gehrig's disease or classical motor neuron disease, is the most common form of motor neuron disease (MND), with both upper and lower motor neuron involvement. This form of the disease is characterized by weakness and wasting in the limbs. Muscle weakness and atrophy occur on both sides of the body. Affected individuals lose strength and the ability to move their arms and legs, and to hold the body upright. Other symptoms include spasticity, spasms, muscle cramps, and fasciculations. Speech can become slurred or nasal. When muscles of the diaphragm and chest wall fail to function properly, individuals lose the ability to breathe without mechanical support. Although the disease does not usually impair a person's mind or personality, several recent studies suggest that some people with ALS may develop cognitive problems involving word fluency, decision-making, and memory. Most individuals with ALS die from respiratory failure, usually within 3 to 5 years from the onset of symptoms. Complex pathophysiology of ALS presents many potential therapeutic targets. However, although a wide range of agents has been investigated, only Riluzole (Rilutek®), an inhibitor of glutamate release, has demonstrated consistent benefits, and is the only approved drug for the treatment of the disease.

But Riluzole's benefits are modest—it prolongs survival in ALS patients for several months (~7%) with minimal effect on functional measures. At present, ALS remains a disease for which limited effective treatment options are available. There is clearly an unmet need for more beneficial agents acting through others mode of action: growth factors, ionic alterations, inflammation, mitochondrial alteration, apoptosis . . . .

Huperzine A, a sesquiterpene alkaloid, is isolated from the Chinese club moss *Huperzia serrata* also known as *Lycopodium serratum*. The plant contains mainly alkaloids, triterpenes, flavones, and phenolic acids. Four major structural classes of *Lycopodium* alkaloids have been described, including lycopodine, lycodine (to which huperzine A belongs), fawcettimines, and others.

Huperzine A and huperzine B are potent acetylcholinesterase inhibitors and a promising therapeutic approach in Alzheimer's disease. Huperzine A has been studied for potential use in treating Alzheimer disease and other CNS disorders [Xu et al., Acta Phamacol. Sin. (1999), 20:486-49; Wang et al., J Neural Transm 2009, 116: 457-465]. The results indicate that huperzine A is well-tolerated and beneficial for Alzheimer's disease patients, particularly when administered at a daily dose of 300-500 µg [Wang et al. 2009, already cited; Xing et al. Evidence-Based Complementary and Alternative Medicine, volume 2014, Article ID 363985, 10 pages]. In addition to its acetylcholinesterase inhibitory effect, huperzine A possesses different other pharmacological effects. These noncholinergic roles, for instance the antagonistic effect on NMDA receptor, the protection of neuronal cells against 62-amyloid, free radicals and hypoxia-ischemia-induced injury, could be important in AD treatment. Growing studies have indicated that a range of Chinese herbs or herbal extracts such as green tea polyphenols or catechins, *panax ginseng* and ginsenoside, *ginkgo biloba* and EGb 761, *polygonum*, triptolide from *triptery-gium wilfordii* hook, polysaccharides from the flowers of *nerium* indicum, oil from *ganoderma lucidum* spores, huperzine and stepholidine are able to attenuate degeneration of dopamine neurons and symptoms caused by the neurotoxins 1-methyl-4-phenyl-1,2,3,6-tetrahydropyridine (MPTP) and 6-hydroxydopamine (6-OHDA) in vitro and in vivo conditions. In addition, accumulating data have suggested that Chinese herbs or herbal extracts may promote neuronal survival and neurite growth, and facilitate functional recovery of brain injuries [Liang-Wei Cheng et al. in CNS & Neurological Disorders—Drug Targets (Formerly Current Drug Targets—CNS & Neurological Disorders), 2007, 6(4), 273-281].

Animal and clinical studies showed that huperzine A, when administered orally, is absorbed rapidly, distributed throughout the body and eliminated at a moderate rate, and that huperzine A has a lower toxicity compared to other drugs such as tacrine which has significant hepatotoxic potential.

Huperzine B (HupB), the minor alkaloid in the plant *Huperzia serrata* and a structural sibling of huperzine A, is less potent and selective in the inhibition of AChE than HupA. However, it possesses a higher therapeutic index than huperzine A that is in agreement with its longer duration of action. In behavioural studies, HupB improved memory retention and memory retrieval in adult and aged mice, and reversed the disruption of memory retention induced by scopolamine, sodium nitrite, electroconvulsive shock, and cycloheximide in mice [Zhu X. D. et al., Acta Pharmacol. Sin. (1988) 9(6): 492-497]. Recent studies also revealed new 16-substituted derivatives of HupB that exert neuroprotective effects by attenuating hydrogen peroxide-induced neurotoxicity [Shi et al., Acta Pharmacologica Sinica (2009) 30: 1195-1203].

There are a number of synthetic huperzine A analogs. Huprine X for example is a fusion product that combines the carbobicyclic substructure of huperzine A with the 4-aminoquinoline substructure of tacrine [Badia A et al, Bioorg Med Chem 1998, 6:427-440]. Another synthetic analog is ZT-1, which is a prodrug that, in the body, is progressively hydrolysed into huperzine A [Li et al, Biomed Chromatogr 2008, 22:354-360]. These "hybrid" products are of interest because they may be effective at lower doses and, therefore, cause fewer side effects.

Hydroxycinnamic acids are phenolic phytochemicals present in fruits, vegetables, and coffee. This group of polyphenols includes caffeic acid, ferulic acid, chlorogenic acid, isoferulic acid and coumaric acid, which are known to exert beneficial effects linked to their antioxidant activity.

Ferulic acid, also named as 4-hydroxy-3-methoxy cinnamic acid, is a phenol acid widely found in a variety of plants. Ferulic acid has a wide range of pharmacological effects such as anti-inflammatory effect, antibacterial effect, antioxidant effect and antitumor effect. Among its various benefits, much interest has been focused on the suppressive effect of ferulic acid on Alzheimer's disease [Nakamura, S. et al., Geriat. Med. 46, 1511-1519 (2008)].

Caffeic acid, a hydroxycinnamic acid derivative has antioxidant, anti-inflammatory, analgesic and immunomodulatory effects. Literature also reports the neuroprotective effects of caffeic acid [Anwar J. et al., Pharmacol Biochem Behav; 2:386-394 (2012), Jeong C H et al., Chin Med, 6:25 (2011)].

Although huperzines as well as hydroxycinnamic acids have been used separately in clinical trials for treatment of neurodegenerative diseases, no studies have evaluated the effect of compositions combining huperzine and hydroxycinnamic acids on Alzheimer's disease.

WO2011/132157 discloses sustained-release formulations comprising huperzine A and methods utilising said formulations for treating a medical condition such as Alzheimer's disease.

EP2343065 A1 discloses a composition comprising a combination of ferulic acid and matrine compounds and its therapeutic use for treating various diseases such as Alzheimer's disease.

WO2008/108825 discloses pharmaceutical compositions comprising a neuroprotective amount of a compound selected in particular from members of the group consisting of para carnosic acid, para L-dopa, para caffeic acid or a pharmaceutically acceptable prodrug, salt or solvate thereof.

Thus, none of the above mentioned prior arts disclose a specific combination of huperzine and hydroxycinnamic acids.

In this context, the inventors have shown for the first time that huperzine and hydroxycinnamic acids have synergistic effects when used in combination for the treatment of Alzheimer's disease. They investigated the neuroprotective effect of a plant extract of *Huperzia serrata* on rat primary cortical neurons injured with glutamate as in vitro model of AD. In light of the obtained results and an analytical analysis of the chemical profile of the extract, they identified three compounds potentially involved in the neuroprotective effect: huperzine A, caffeic acid and ferulic acid. The synergistic effect of these compounds was also investigated.

The effect of said compounds was further investigated in a second in vitro model of AD which is β-amyloid peptide injured primary cortical neurons.

Therefore one object of the present invention is to provide a combination composition for treatment of Alzheimer's disease and other CNS disorders and a preparation method thereof.

According to the present invention, a combination composition is provided comprising as active components, in synergistically effective amounts (i) a huperzine of natural or synthetic origin or a plant extract containing huperzine, and (ii) at least two compounds selected from the group consisting of hydroxycinnamic acids, anthoxanthins and anthocyanins of natural or synthetic origin, mixtures thereof and a plant extract containing same.

The huperzine is selected from the group consisting of huperzine A, huperzine B, analogs thereof and mixtures thereof. According to the invention, the composition may contain huperzine A alone or huperzine B alone or an analog thereof alone or a combination of two or more of huperzine A, huperzine B and analogs.

The active compounds may be used as such or under the form of physiologically acceptable salts.

The active components may be naturally occurring or synthetic. Non-naturally occurring active agents may suitably be prepared by modification of side groups and/or side atoms of naturally occurring compounds, as known in the art.

Extracts of plant in particular *Huperzia serrata* extract may also be used. Thus, according to the present invention, said combination composition may be an aqueous or an organic mixture of said active components or a plant extract. Such extracts may be prepared by any technics known in the art.

According to a preferred embodiment of the present invention, the at least two compounds (ii) are two hydroxcinnamic acids of natural or synthetic origin. According to the Invention, the hydroxycinnamic acids are selected from the group comprising or consisting of α-cyano-4-hydroxycinnamic acid, caffeic acid, cichoric acid, cinnamic acid, chlorogenic acid, diferulic acids, coumaric acid, coumarin, ferulic acid, sinapinic acid.

According to a most preferred embodiment, the hydroxycinnamic acids are caffeic acid and ferulic acid. Advantageously, the huperzine, in particular huperzine A, the caffeic acid and the ferulic acid may be used in different ratios, e.g., at a molar ratio huperzine/caffeic acid/ferulic acid; for example it may be comprised between from 0.01/0.5/10 to 0.1/5/1000, preferentially between from 0.01/0.5/10 to 0.1/0.5/1000, advantageously equal to 0.01/0.5/100; another possible ratio is 0.01/50/100 or 0.01/5/100. It will be understood that the amount of the drug actually administered will be determined by a physician, in the light of the relevant circumstances including the condition or conditions to be treated, the exact composition to be administered, the age, weight, and response of the individual patient, the severity of the patient's symptoms, and the chosen route of administration. Therefore, the above dosage ranges are intended to provide general guidance and support for the teachings herein, but are not intended to limit the scope of the invention. An advantage of the invention is that each compound may be used at low doses in a combination therapy, while producing, in combination, a substantial clinical benefit to the subject. The combination therapy may indeed be effective at doses where the compounds have individually low or no effect. Accordingly, a particular advantage of the invention lies in the ability to use sub-optimal doses of each compound, i.e., doses which are lower than therapeutic doses usually prescribed, preferably ½ of therapeutic doses, more preferably ⅓, ¼, ⅕, or even more preferably ¹⁄₁₀ of therapeutic doses. In particular examples, doses as low as ¹⁄₂₀, ¹⁄₃₀, ¹⁄₅₀, ¹⁄₁₀₀, or even lower, of therapeutic doses are used. At such sub-therapeutic dosages, the compounds would exhibit no side effect, while the combination(s) according to the invention are fully effective for treatment of Alzheimer's disease and other CNS disorders.

According to another object of the present invention, there is provided a combination composition such as described before for its use in preventing, inhibiting, retarding or treating neuronal degeneration in a subject suffering from a neurodegenerative disease or condition.

More particularly the invention provides a combination composition for its use in preventing inhibiting, retarding or treating a subject suffering from a disease or condition selected from the group consisting of: Alzheimer's disease (AD), senile dementia of AD type (SDAT), Parkinson's disease, Lewis body dementia, vascular dementia, autism, myasthenia gravis, Lambert Eaton disease, mild cognitive impairment (MCI), age-associated memory impairment (AAMI) and problem associated with ageing, (i) non-cognitive neurodegeneration, (ii) non-cognitive neuromuscular degeneration, (iii) motor-sensory neurodegeneration, or (iv) receptor dysfunction or loss in the absence of cognitive, neural and neuromuscular impairment, in a human or non-human animal subject suffering from, or susceptible to, any of Parkinson's disease, postencephalitic Parkinsonism, depression, schizophrenia, muscular dystrophy including facioscapulohumeral muscular dystrophy (FSH), Duchenne muscular dystrophy, Becker muscular dystrophy and Bruce's muscular dystrophy, Fuchs' dystrophy, myotonic dystrophy, corneal dystrophy, reflex sympathetic dystrophy syndrome (RSDSA), neurovascular dystrophy, Huntington's disease, motor neurone diseases including amyotrophic lateral sclerosis (ALS), multiple sclerosis, postural hypotension, traumatic neurodegeneration, Batten's disease, Cockayne syndrome, Down syndrome, corticobasal ganglionic degeneration, multiple system atrophy, cerebral atrophy, olivopontocerebellar atrophy, dentatorubral atrophy, pallidoluysian atrophy, spinobulbar atrophy, optic neuritis, subacute sclerosing panencephalitis (SSPE), attention deficit disorder, post-viral encephalitis, post-poliomyelitis syndrome, Fahr's syndrome, Joubert syndrome, Guillain-Barre syndrome, lissencephaly, Moyamoya disease, neuronal migration disorders, autistic syndrome, polyglutamine disease, Niemann-Pick disease, progressive multifocal leukoencephalopathy, pseudotumor cerebri, Refsum disease, Zellweger syndrome, supranuclear palsy, Friedreich's ataxia, spinocerebellar ataxia type 2, Rhett syndrome, Shy-Drager syndrome, tuberous sclerosis, Pick's disease, chronic fatigue syndrome, neuropathies including hereditary neuropathy, diabetic neuropathy and anti-mitotic neuropathy, prion-based neurodegeneration, including Creutzfeldt-Jakob disease (OD), variant CJD, new variant CJD, bovine spongiform encephalopathy (BSE), GSS, FFI, kuru and Alper's syndrome, Joseph's disease, acute disseminated encephalomyelitis, arachnoiditis, vascular lesions of the central nervous system, loss of extremity neuronal function, Charcot-Marie-Tooth disease, susceptibility to heart failure, asthma, and macular degeneration. The composition is particularly useful for the treatment and prevention of Alzheimer disease.

According to still another object of the present invention, there is provided a method for preventing, inhibiting, retarding or treating neuronal degeneration in a subject in need thereof, wherein the method comprises administering an effective amount of the composition according to the invention to said subject.

As described herein, the combination compositions according to the present invention may be prepared as pharmaceutical compositions, especially pharmaceutical compositions useful for the treatment of Alzheimer's disease. Such compositions may comprise the active compounds (i) and (ii) as defined above together with a pharmaceutically acceptable excipient.

According to a further aspect of the present invention, the combination composition may be prepared as neutraceutical compositions comprising the active compounds (i) and (ii) as defined above together with a nutraceutically acceptable excipient.

The combination composition according to the present invention can be formulated for oral administration, topical administration, transdermal administration, parenteral administration and combinations thereof.

Suitable forms for oral administration include tablets, compressed or coated pills, dragées, sachets, troches, granulates, hard or soft gelatin capsules, sublingual tablets, syrups, solutions, and suspensions, aerosols; for parenteral administration the invention provides ampoules or vials that include an aqueous or non-aqueous solution or emulsion; for rectal administration there are provided suppositories with hydrophilic or hydrophobic vehicles; and for topical application as ointments and transdermal delivery there are provided suitable delivery systems as known in the art for example patches.

The preferred dosages of the active ingredients in the above compositions will be defined by the one skilled in the art on the basis of his general knowledge. Said dosages may be taken daily in one or several outlet.

In accordance with the present invention, the composition may be formulated for immediate release, extended release or timed release.

According to a further aspect of the invention, the combination composition may be for simultaneous, separate or sequential use in treating or preventing a neurodegenerative disease or condition.

The invention further provides an extract of *Huperzia serrata* comprising huperzine A/caffeic acid/ferulic acid at a molar ratio at a molar ratio comprised between from 1/0.1/0.1 to 1/0.4/0.6, preferentially at a molar ratio of 1/0.1/0.5. Such an extract has good therapeutic effect and is suitable for simultaneous, separate or sequential use in treating or preventing a neurodegenerative disease or condition.

The invention will now be described in more detail in the following non-limiting examples and their accompanying FIGS. 1 to 11.

FIG. 1 illustrates the effect of *Huperzia serrata* (HS) extract (N6001-1) at different concentrations on the toxicity of glutamate (40 μM, 20 min) on primary cortical neuron survival (a) and neurite network (b) injured by glutamate (40 μM, 20 min). Data were expressed as percentage of control as mean±SEM (100%=no glutamate). * $p<0.05$ vs glutamate (one way ANOVA followed by Dunnett's test). The amount of huperzine A (HA or Hpz A) in each extract was indicated for each extract concentration.

FIG. 2a illustrates the effect of Huperzine A (HA) at different concentrations on the toxicity of glutamate (40 μM, 20 min) on neurite network. Data were expressed as percentage of control as mean±SEM (100%=no glutamate). * $p<0.05$ vs glutamate (one way ANOVA followed by PLSD Fisher's test). Hup A means Huperzine A.

FIG. 2b illustrates the effect of Huperzine A (HA) at different concentrations on the toxicity of glutamate (40 μM, 20 min) on primary cortical neuron. Data were expressed as percentage of control as mean±SEM (100%=no glutamate). * $p<0.05$ vs glutamate (one way ANOVA followed by PLSD Fisher's test). Hup A means Huperzine A.

Figure 6:
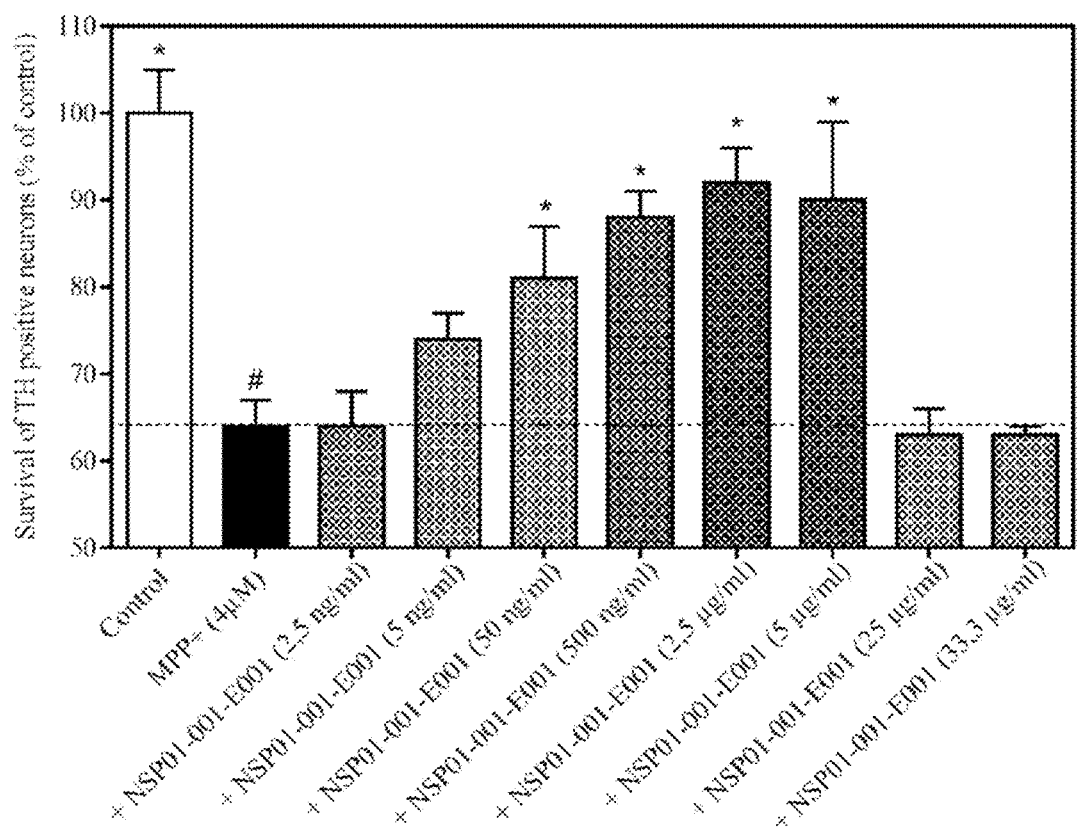

FIG. 6 illustrates the effect of MPP$^+$ (4 μM, 48 hours) in presence or absence of NSP01-001-E001 at different concentrations on TH positive dopaminergic neuron survival of primary mesencephalic culture. Data were expressed as percentage of control as mean±SEM (100%=no MPP$^+$). # $p<0.05$ Control vs MPP$^+$ group; * $p<0.05$ vs MPP$^+$ (one-way ANOVA followed by Dunnett's and PLSD Fisher's test).

FIGS. 7 a-d illustrate the effect of MPP$^+$ (4 μM, 48 hours) in presence or absence of Huperzine A (HA) (FIG. 7a), caffeic acid (CA) (FIG. 7b), ferulic acid (FA) (FIG. 7c) or mixtures thereof (FIG. 7d) at different concentrations on TH positive dopaminergic neuron survival of primary mesencephalic culture. Data were expressed as percentage of control as mean±SEM (100%=no MPP$^+$). # $p<0.05$ Control vs MPP$^+$ group; * $p<0.05$ vs MPP$^+$ (one way ANOVA followed by PLSD Fisher's test).

FIGS. 8 a-h illustrate the effect of Glutamate (40 μM, 20 min) in presence or absence of sinapic acid (SA), paracoumaric acid (pCouA), gallic acid (GA) and/or Huperzine A (HA) at different concentrations on primary cortical neuron survival (FIGS. 8a, 8c, 8e and 8g) and neurite network (FIGS. 8b, 8d, 8f and 8h). Data were expressed as percentage of control as mean±SEM (100%=no glutamate). * $p<0.05$ vs glutamate, # $p<0.05$ glutamate vs control (one way ANOVA followed by PLSD Fisher's test).

FIGS. 9 a-d illustrate the effect of glutamate (60 μM, 20 min) in presence or absence of Huperazine A (HA) (FIG. 9a), Caffeic Acid (CA) (FIG. 9b), Ferulic Acid (FA) (FIG. 9c), or a mixture thereof (FIG. 9d) on NMJ area (mean size). Data were expressed as percentage of control as mean±SEM (100%=no glutamate). * $p<0.05$ vs glutamate group.

FIGS. 10 a-d illustrate the effect of glutamate (60 μM, 20 min) in presence or absence of Huperazine A (HA) (FIG. 10a), Caffeic Acid (CA) (FIG. 10b), Ferulic Acid (FA) (FIG. 10c), or a mixture thereof (FIG. 10d) on neurite network (area of innervation). Data were expressed as percentage of control as mean±SEM (100%=no glutamate). * $p<0.05$ vs glutamate group.

Figure 11:
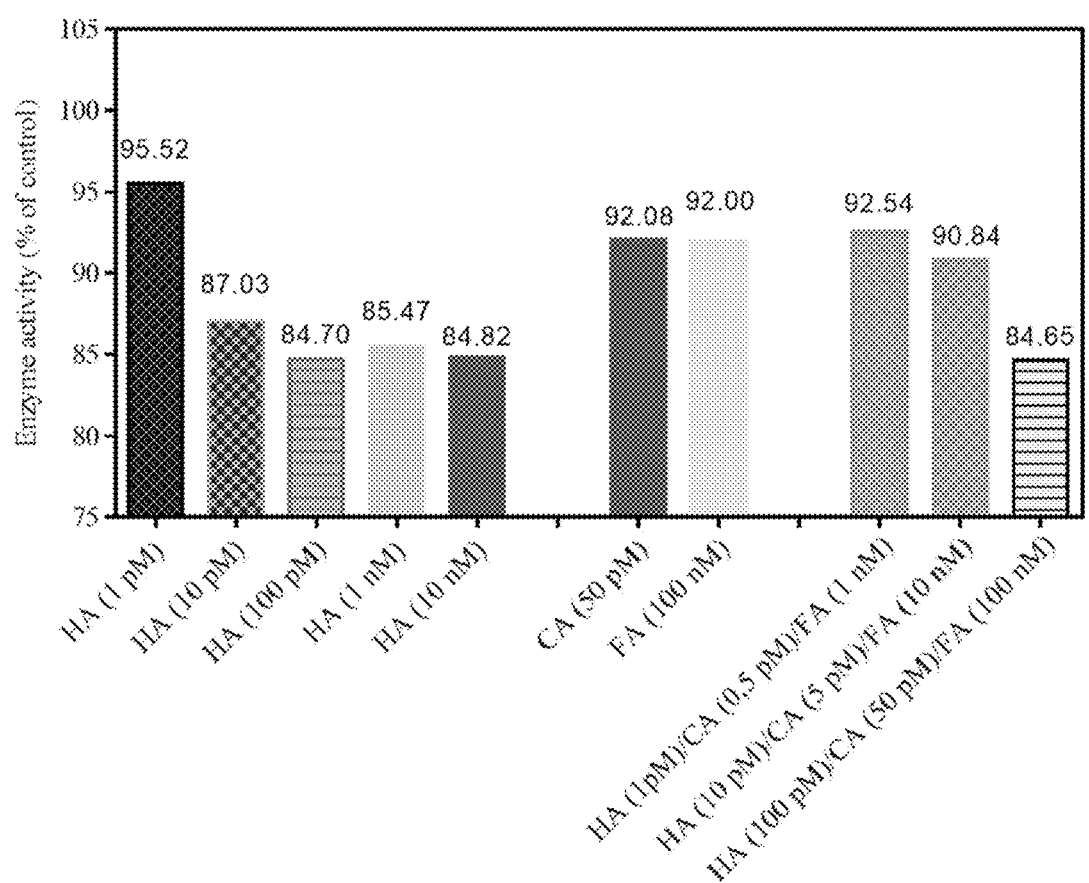

FIG. 11 illustrates the effect of either Huperazine A (HA) at different doses, Caffeic Acid (CA) at 50 pM, Ferulic Acid (FA) at 100 nM, or mixture thereof at different ratios on the activity of the Acetylcholinesterase. (AChE).

Figure 12:
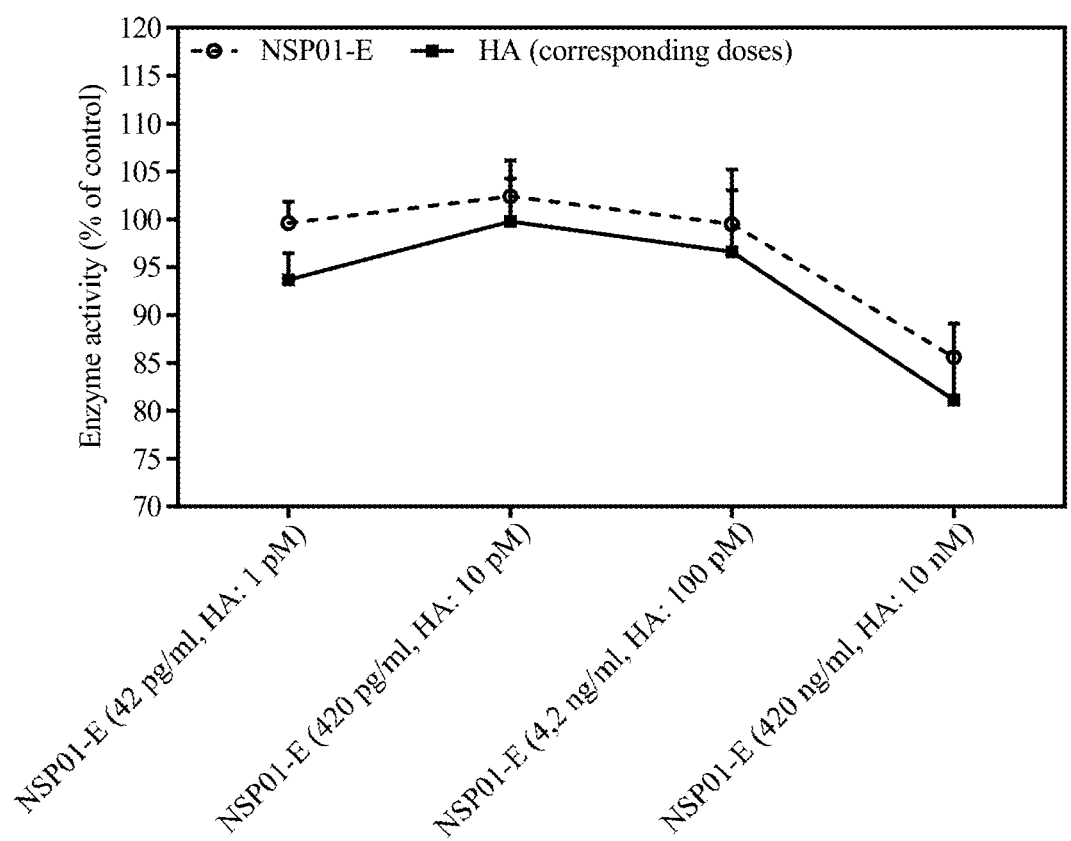

FIG. 12 illustrates the dose effect of HA and NSP01-E (NSP01-001-E001) on Acetylcholinesterase activity—the dose of HA alone is the equivalent dose of the one found in the NSP01-E.

EXAMPLE 1: PREVENTION OF GLUTAMATE TOXICITY ON NEURONAL CELLS BY *HUPERZIA SERRATA* (HS) EXTRACTS

Glutamate excitotoxicity is responsible for neuronal death in acute neurological disorders including neurodegenerative disease. Loss of calcium homeostasis is a key mediator of glutamate-induced cell death. The inventors tested extracts from *Huperzia serrata* for their ability to prevent or reduce the toxic effects of glutamate on primary cortical neurons injured by glutamate.

1. Experimental Section

*Huperzia serrata* (HS) extracts are obtained from dried plant material by several methods, including conventional reflux, ultrasound and microwave assisted extraction, as described by Zha Shenghua et al. and Sun Yuan-Ming et al. [Zha Shenghua et al., Natural Product Research and Development (2005) 17(1):7-10; Sun Yuan-Ming et al., Chinese Traditional and Herbal Drugs (2002) 33(12):1078-1092]. The solvent used here was pure water. An analytical method based on HPLC was used to dose the huperzine A (HA) and polyphenolic acids in each extract performed.

HA/CA/FA ratios obtained from various methods of extractions are shown in Table 1 below.

TABLE 1

HA/CA/FA ratios obtained from various methods of extractions.

| Huperzia serrata extract | HA/CA/FA ratio in extract | Activity |
|---|---|---|
| N6001-1 | 1/0.1/0.2 | + |
| N6001-2 | 1/0.4/0.3 | + |
| N6001-3 | 1/0.3/0.4 | + |
| N6001-6 | 1/0.2/0.5 | + |
| N6001-7 | 1/0.3/0.1 | + |
| N6001-8 | 1/0.3/0.1 | + |
| N6002-5 | 1/0.5/0.06 | − |

The neuroprotective effect of HS extract was assessed by quantification of the neurite network which specifically reveals the glutamatergic neurons.

Rat cortical neurons were cultured as described by Singer et al., 1999 [J. Neuroscience 19(7), 2455-2463] and Callizot et al. 2013 [J. Neurosc. Res. 91(5), 706-716].

Briefly, pregnant females (Wistar; JanvierLabs, St Berthevin, France) at 15 days of gestation were killed by cervical dislocation. Foetuses were collected and immediately placed in ice-cold L15 Leibovitz medium (Pan Biotech, Aidenbach, Germany, Batch: 4120413) with a 2% penicillin (10,000 U/ml) and streptomycin (10 mg/ml) solution (PS; Pan Biotech, Aidenbach, Germany) and 1% bovine serum albumin (BSA; Pan Biotech, Aidenbach, Germany). Cortex was treated for 20 min at 37° C. with a trypsin-EDTA (Pan Biotech, Aidenbach, Germany) solution at a final concentration of 0.05% trypsin and 0.02% EDTA. The dissociation was stopped by addition of Dulbecco's modified Eagle's medium (DMEM) with 4.5 g/liter of glucose (Pan Biotech, Aidenbach, Germany), containing DNAse I grade II (final concentration 0.5 mg/ml; Pan Biotech, Germany) and 10% fetal calf serum (FCS; Invitrogen, Cergy Pointoise, France). Cells were mechanically dissociated by three forced passages through the tip of a 10-ml pipette. Cells were then centrifuged at 515 g for 10 min at 4° C. The supernatant was discarded, and the pellet was resuspended in a defined culture medium consisting of Neurobasal medium (Invitrogen, Cergy Pointoise, France) with a 2% solution of B27 supplement (Invitrogen, Cergy Pointoise, France), 2 mmol/liter of L-glutamine (Pan Biotech, Aidenbach, Germany), 2% of PS solution, and 10 ng/ml of brain-derived neurotrophic factor (BDNF; Pan Biotech, Aidenbach, Germany). Viable cells were counted in a Neubauer cytometer, using the trypan blue exclusion test. The cells were seeded at a density of 30,000 per well in 96-well plates precoated with poly-L-lysine (Corning Biocoat, Tewksbury, USA) and were cultured at 37° C. in an air (95%)-CO2 (5%) incubator. The medium was changed every 2 days.

On day 13, the cultures were exposed for 20 minutes to glutamate 40 µM in the absence or presence of *Huperzia serrata* extracts. Then the cells were washed out and new fresh medium containing or not *Huperzia serrata* extracts was added for another 48 hours.

The cells were then fixed by a cold solution ethanol/acetic acid (95:5 v/v) for 5 minutes at −20° C. After permeabilization with 0.1% of saponin (Sigma), cells were incubated for 2 hours with mouse monoclonal antibody against microtubule-associated-protein 2 (MAP 2; Sigma) at dilution of 1/400 in PBS containing 1% foetal calf serum (Invitrogen) and 0.1% of saponin. This antibody was revealed with Alexa Fluor 488 goat anti-mouse IgG (Invitrogen) at the dilution of 1/400 in PBS containing 1% foetal calf serum and 0.1% of saponin for 1 hour at room temperature.

Neuron survival assessment: For each condition 6 wells were assessed, 20 pictures per well were taken using InCell Analyzer™ 1000 (GE Healthcare) with 20× magnification to assess cell bodies (MAP 2 staining). Analysis of picture was done using Developer software (GE Healthcare), the number of neurons per picture was recorded. A mean of neuron number of the 20 pictures was automatically calculated per well, then one data was provided per well (total of 6 raw data were provided per condition).

Neurite network length assessment: For each condition 6 wells were assessed, 20 pictures per well were taken using InCell Analyzer™ 1000 with 20× magnification (20 pictures at X20 representing ~80% of the total well surface), to assess MAP-2 staining. Analysis of picture was done using Developer software, the total neurite length per picture was recorded. A mean neurite length of the 20 pictures was automatically calculated per well, then one data was provided per well (total of 6 raw data were provided per condition).

2. Results

Figure 1A:
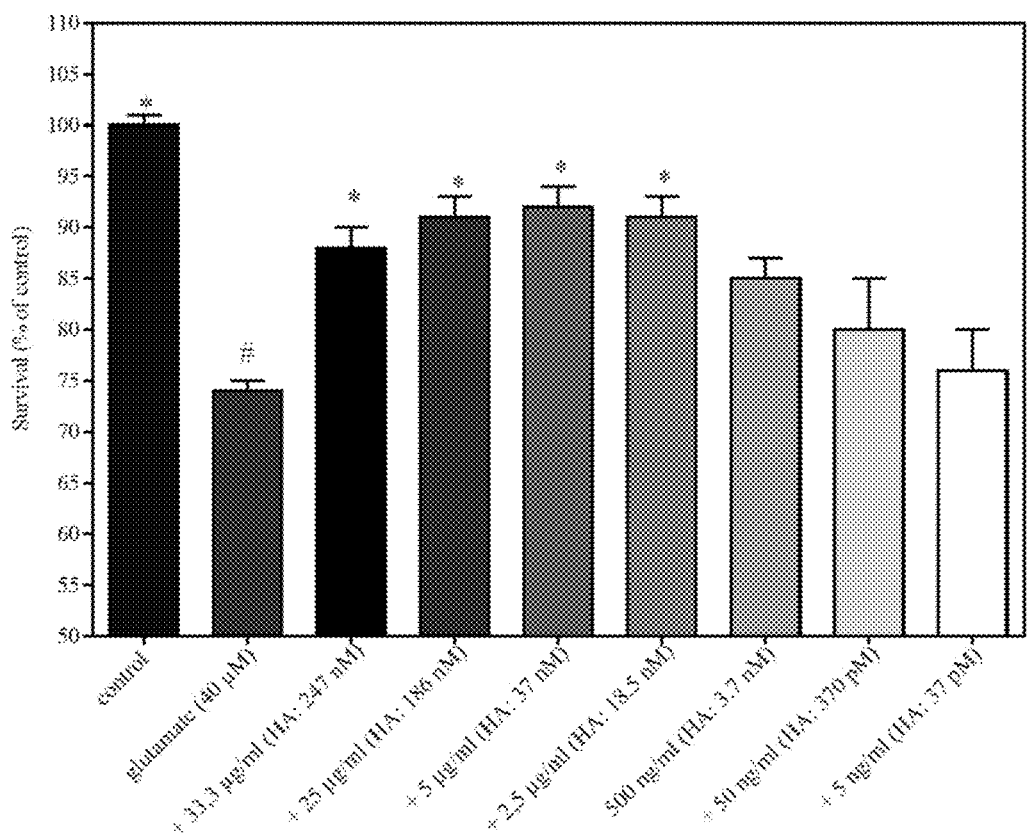

They are given in FIG. 1.

They demonstrate that HS extracts induce a substantial protective effect against the toxicity caused by glutamate.

Figure 1B:
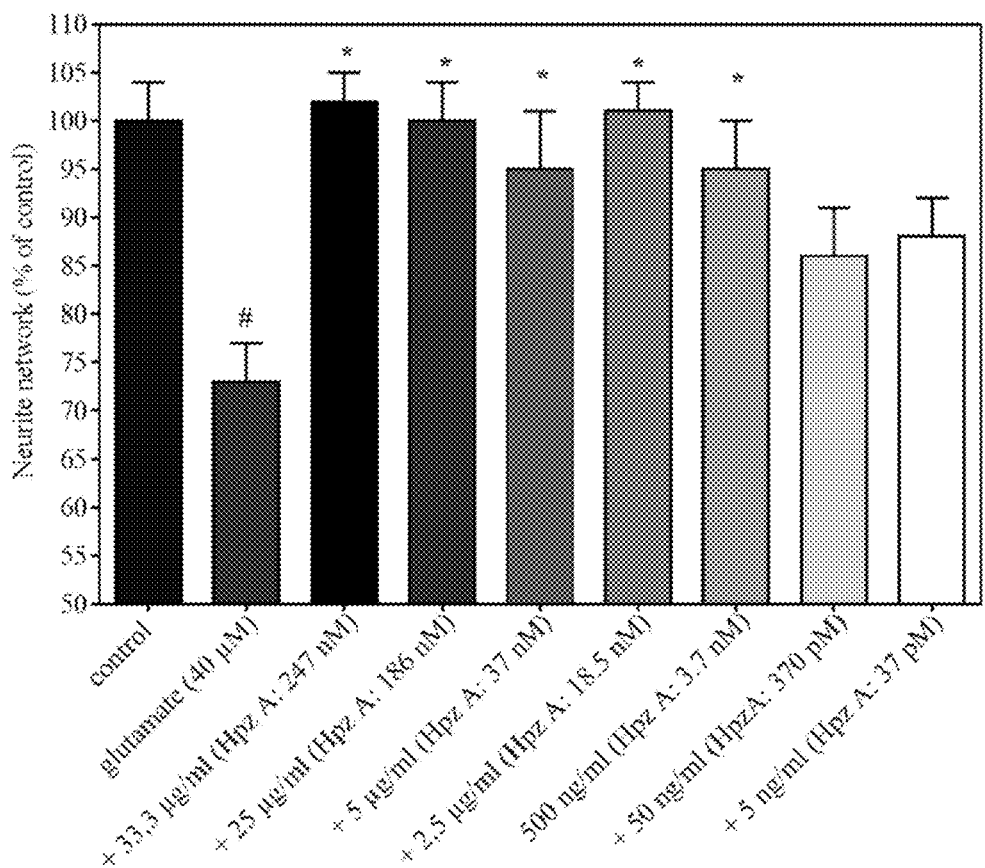

Glutamate (40 µM, 20 min) induced a significant neuronal death (~25%) (FIG. 1a) and a large loss of neurite (by 25%) (FIG. 1b). In presence of the *Huperzia serrata* extract N6001-1 (33.3 µg/ml; 25 µg/ml, 5 µg/ml and 2.5 µg/ml) added 1 hour before the glutamate and let during the toxic application and 48 h after wash-out, a significant protective effect was observed on the neuron survival (~90% of survival) (FIG. 1a) as well as the neurite network (FIG. 1b).

Similar results have been obtained with all extracts whatever the method of extraction except for the extract N6002-5 (in which FA was not present)

EXAMPLE 2: PREVENTION OF GLUTAMATE TOXICITY ON NEURONAL CELLS BY HUPERZINE A, CAFFEIC ACID ET FERULIC ACID

In light of the results with HS extracts and an analytical analysis of the chemical profile of the used HS extract, three compounds potentially involved in the protective effect on neuronal cells were identified: huperzine A, caffeic acid and ferulic acid.

Said candidate compounds have been tested for their ability to prevent or reduce glutamate toxicity on neuronal cells. The compounds were first tested individually, followed by assays of their combinatorial action. The efficacy of the compounds and a combination of them was assessed on primary cortical neuron cells.

1. Experimental Section

The protocol used in these assays is the same as described in example 1. After 13 days of neuron culture, the candidate compounds were solved in DMSO and diluted in culture medium. Candidate compounds were then pre-incubated with cortical neurons 1 hour before the glutamate exposure (20 min, 40 µM) at different concentrations alone or as mixture and let during the toxic application and for another 48 h after wash-out. Candidate compounds were tested on one primary cortical culture in 96 well plates, 6 wells per conditions.

2. Results

Figure 2A:
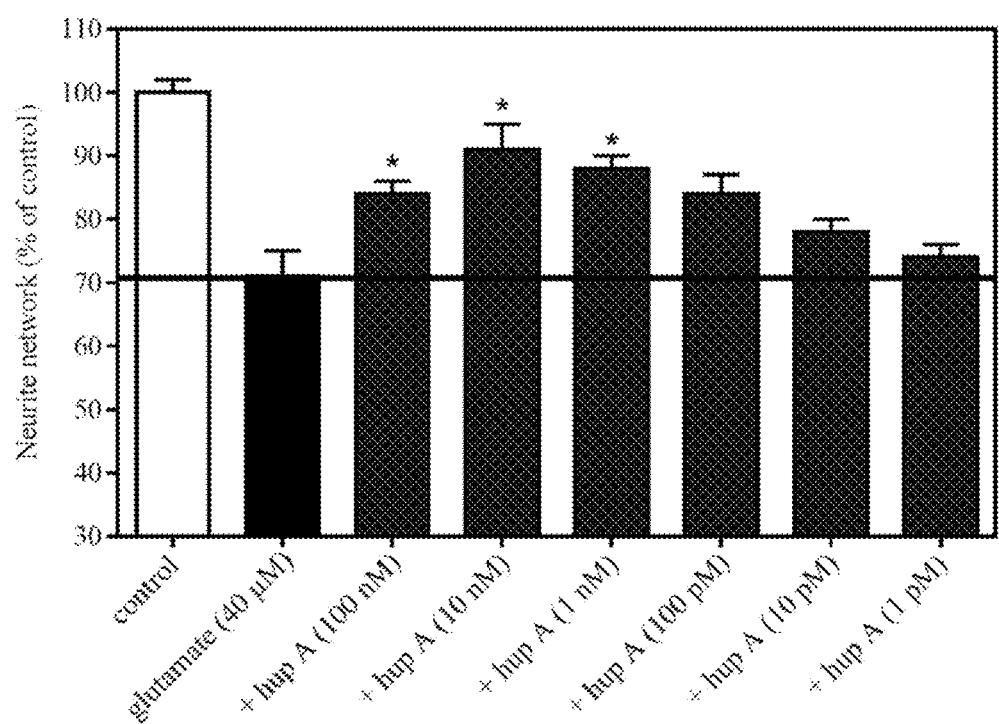
FIG. 2c illustrates the effect of caffeic acid (CA) at different concentrations on the toxicity of glutamate (40 μM, 20 min) on neurite network. Data were expressed as percentage of control as mean±SEM (100%=no glutamate). * $p<0.05$ vs glutamate (one way ANOVA followed by PLSD Fisher's test).
FIG. 2d illustrates the effect of caffeic acid (CA) at different concentrations on the toxicity of glutamate (40 μM, 20 min) on primary cortical neuron survival. Data were expressed as percentage of control as mean±SEM (100%=no glutamate). * $p<0.05$ vs glutamate (one way ANOVA followed by PLSD Fisher's test).
FIG. 2e illustrates the effect of ferulic acid (FA) at different concentrations on the toxicity of glutamate (40 μM, 20 min) on primary cortical neuron survival. Data were expressed as percentage of control as mean±SEM (100%=no glutamate). * $p<0.05$ vs glutamate (one way ANOVA followed by PLSD Fisher's test).
FIG. 2f illustrates the effect of ferulic acid (FA) at different concentrations on the toxicity of glutamate (40 μM, 20 min) on neurite network. Data were expressed as percentage of control as mean±SEM (100%=no glutamate). * $p<0.05$ vs glutamate (one way ANOVA followed by PLSD Fisher's test).
Figure 2B:
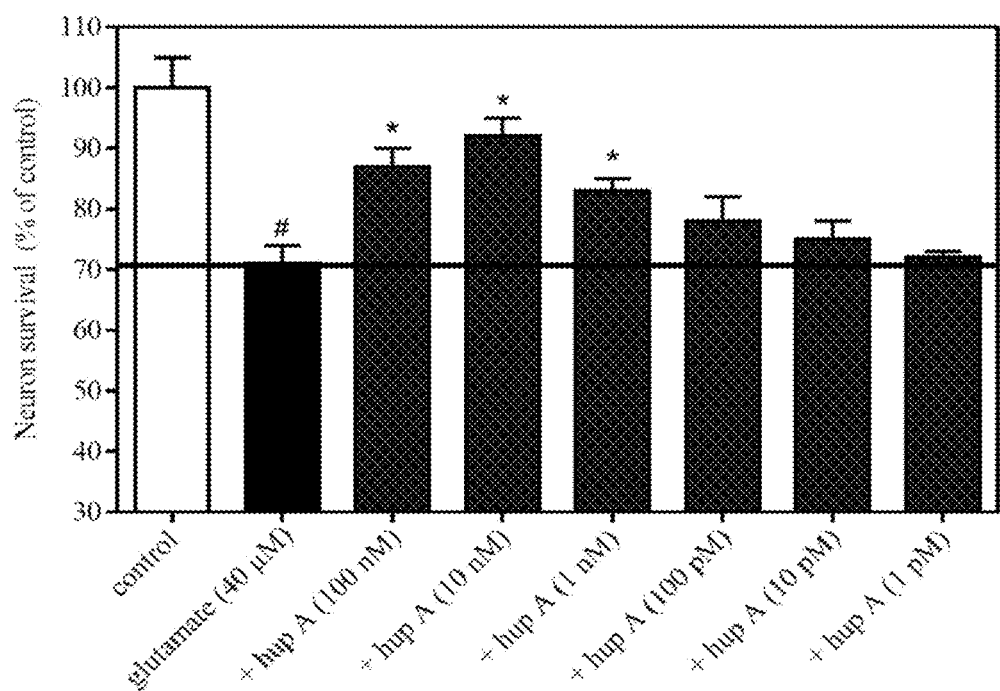
Figure 2C:
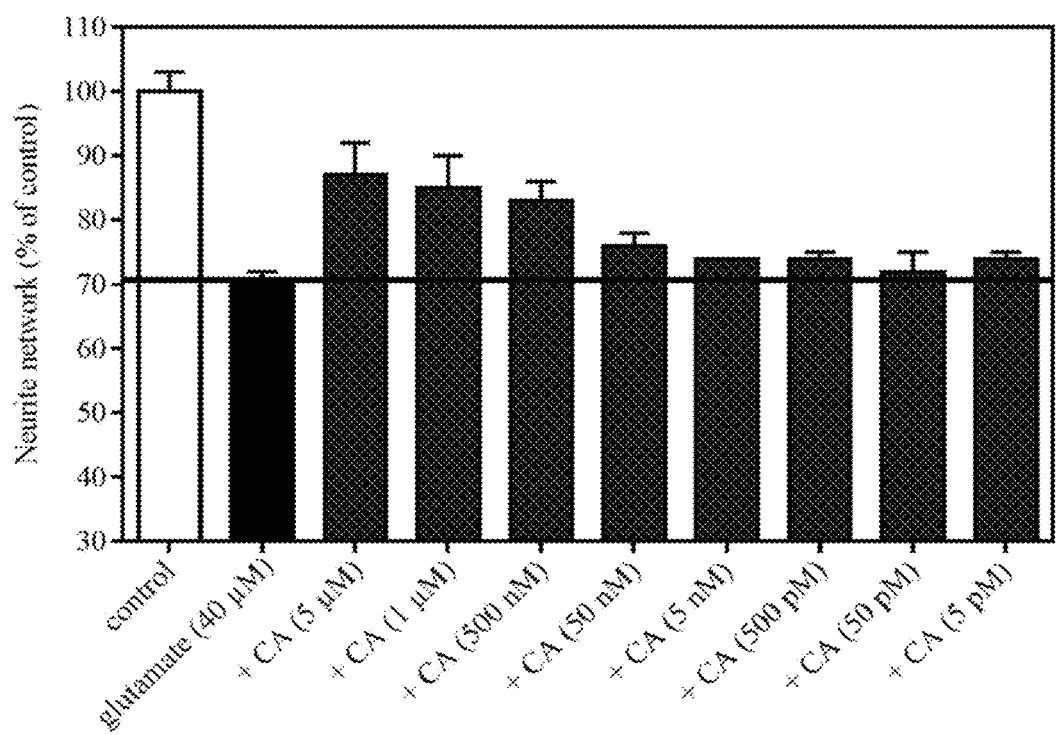
Figure 2D:
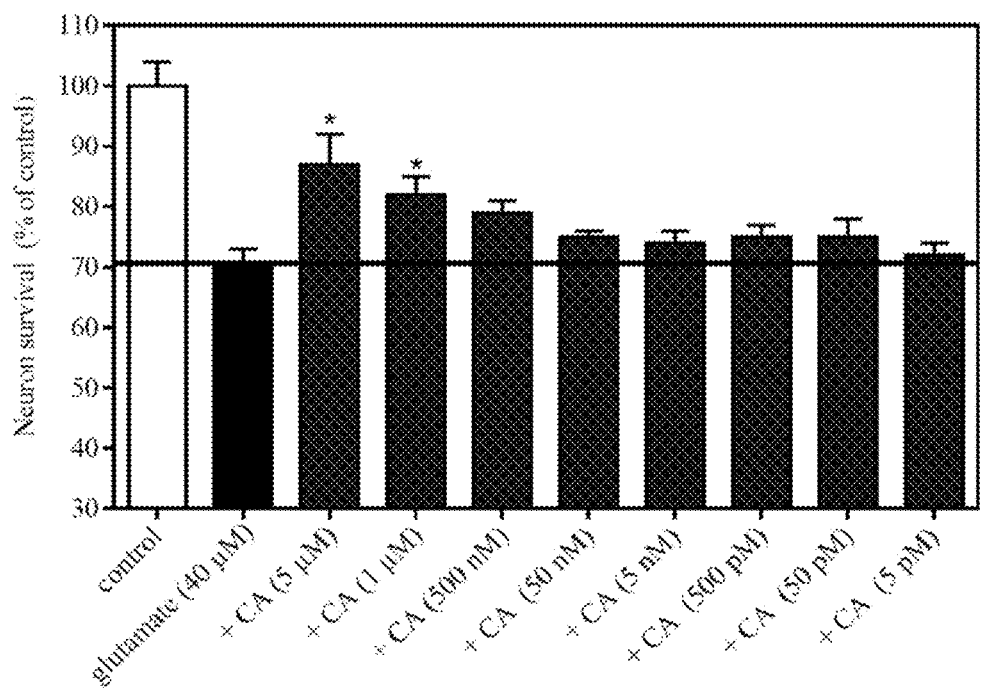
Figure 2E:
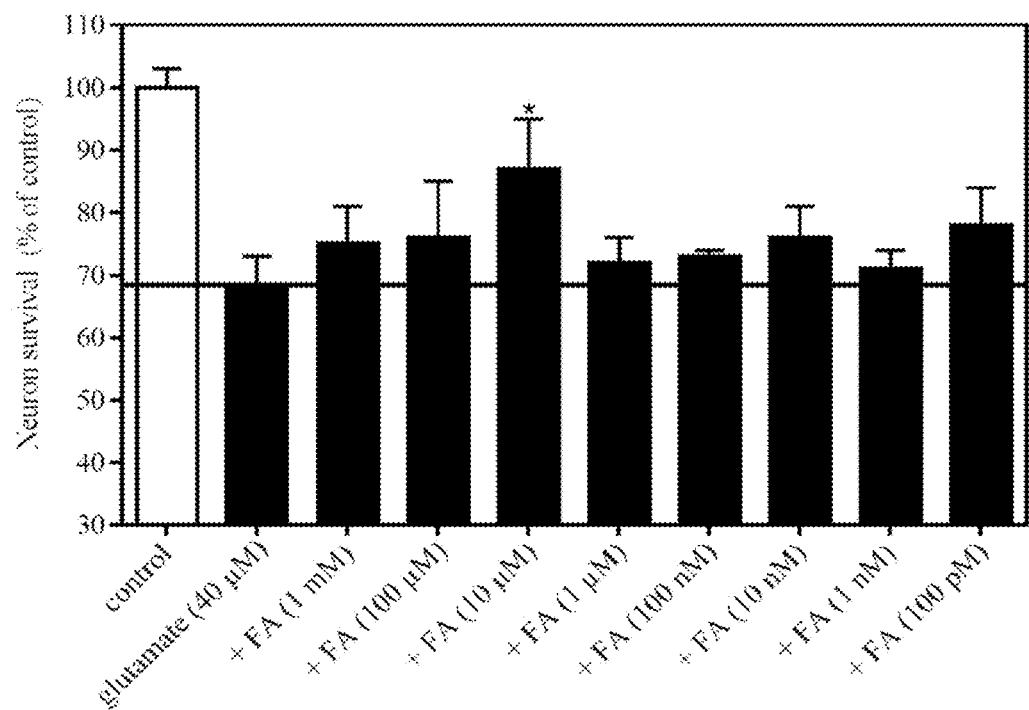
Figure 3A:
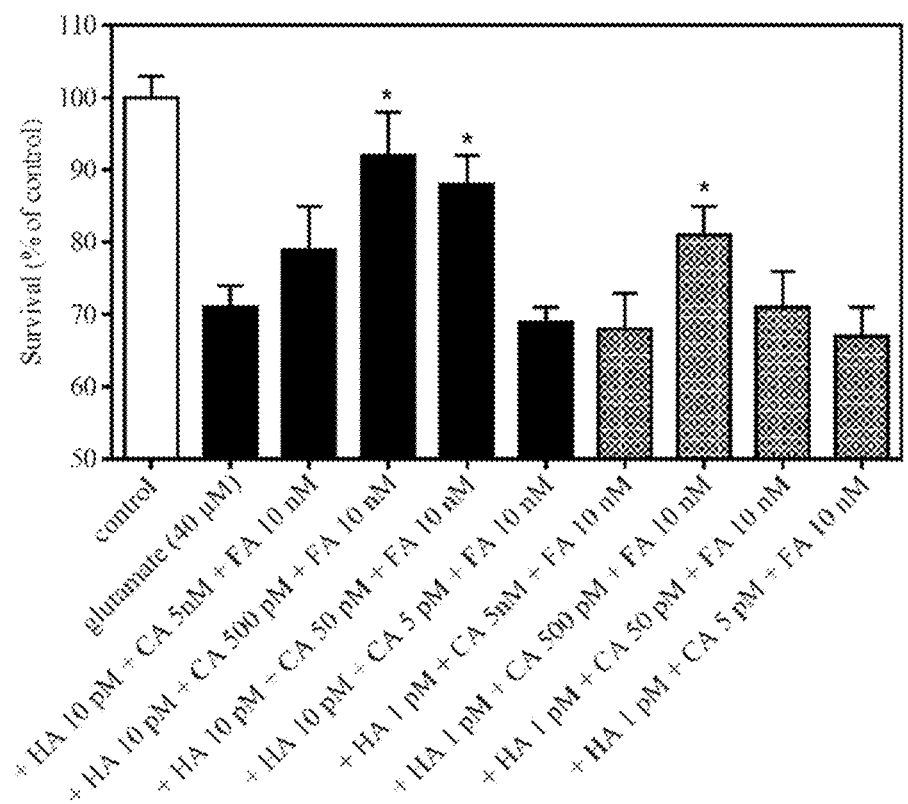
FIG. 3 illustrates the effect of mixtures of huperzine A (HA), caffeic acid (CA) and ferulic acid (FA) at different ratios on the toxicity of glutamate (40 μM, 20 min) on primary cortical neuron survival (a) and neurite network (b). Data were expressed as percentage of control as mean±SEM (100%=no glutamate). * $p<0.05$ vs glutamate (one way ANOVA followed by PLSD Fisher's test).
Figure 3B:
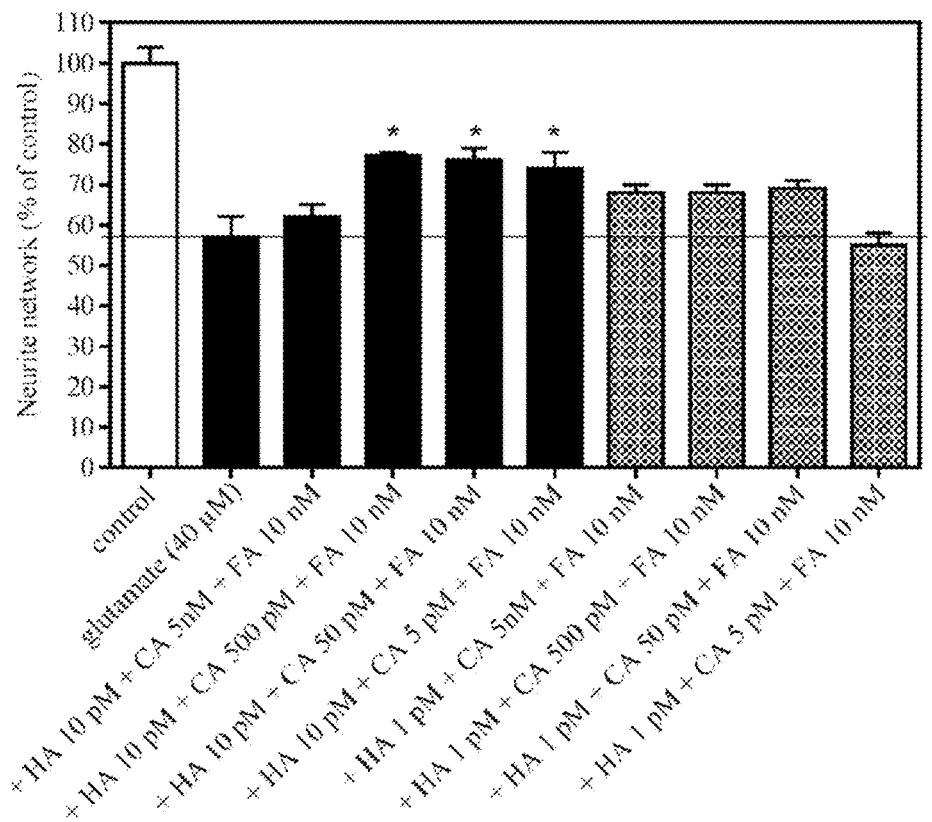

They are shown in FIGS. 2 and 3. They demonstrate that all of the compounds tested alone induce a substantial neuroprotective effect against the toxicity caused by glutamate.

Glutamate (40 μM, 20 min) induced a significant neuronal death (~30%) and a large loss of neurite (by 30%). As shown in FIG. 2:

huperzine A (HA), at a dosage of 10 nM, induces a significant protective effect on the neuron survival (94%) as well as the neurite network (>90%), the lowest active dose was 1 nM (FIG. 2a, b);

caffeic acid (CA), at a dosage of 1 μM and 5 μM, induces a significant protective effect on the neuron survival (>80% of survival) as well as a moderate effect on neurite network (FIG. 2c, d);

ferulic acid (FA), at a dosage of 10 μM and 100 μM, induces a significant protective effect on the neuron survival (>80% of survival) as well as the neurite network (FIG. 2e, f).

The results also show that at the lowest concentrations, HA, CA as well as FA have little or no effect on glutamate toxicity in this model.

As shown in FIG. 3, combinations according to the invention strongly protect neurons from glutamate toxicity under experimental conditions described above.

Glutamate (40 μM, 20 min) induced a significant neuronal death (~30%) and a large loss of neurite (by 40%).

The following mixture concentrations resulted in a significant increase of cortical neuron survival:

10 pM/500 pM/10 nM (HA/CA/FA),
10 pM/50 pM/10 nM (HA/CA/FA) and
1 pM/500 pM/10 nM (HA/CA/FA).

These mixtures were also protective on the neurite network.

In addition, the mixture concentration of 10 pM/5 pM/10 nM (HA/CA/FA) was also protective on neurite network.

A protective effect was also seen with the mixture concentrations 1 pM/5 nM/10 nM (HA/CA/FA), 1 pM/500 pM/10 nM (HA/CA/FA) and 1 pM/50 pM/10 nM (HA/CA/FA) without reaching the significance.

It is noteworthy that an effective protection is noticed using compound concentrations at which compounds used alone were not able to display any protective effect.

For the first time, a synergic protective effect of these compounds was clearly shown.

EXAMPLE 3: PREVENTION OF Aβ-PEPTIDE TOXICITY ON NEURONAL CELLS

In a further series of experiments, the above-identified candidate compounds have been tested for their ability to prevent or reduce the toxic effects of human Aβ1-42 on cortical neurons. Aβ1-42 is the full length peptide that constitutes aggregates found in biopsies from human patients affected with Alzheimer's disease [Sakono et al. 2010, FEBS Journal 277(6), 1348-1358; Callizot et al., 2013, already cited].

1. Experimental Section

The present study used an in vitro model of Alzheimer's disease established by Callizot et al. [2013, already cited], using Aβ-peptide solution containing Aβ-oligomers and permitting to reproduce essential neuropathological features of Alzheimer's disease.

The drugs are first tested individually, followed by assays of their combinatorial action.

The Aβ1-42-preparation was obtained following the procedure described by Callizot et al. [2013, already cited]. Briefly, Aβ1-42 peptide was dissolved in the defined culture medium mentioned above, devoid of serum, at an initial concentration of 40 μmol/liter. This solution was gently agitated for 3 days at 37° C. in the dark and immediately used after being diluted in culture medium to the concentrations used.

On day 11 of culture, HA, CA, FA and mixtures thereof were solved and diluted in culture medium and then pre-incubated with cortical neurons 1 hour before the Aβ1-42-peptide application. Aβ1-42-preparation was then added to a final concentration of 20 μM diluted in control medium.

After 24 hours of Aβ-intoxication, the cultures were fixed and immunolabeled and the neuron survival and the neurite network length were assessed as described in the above example.

2. Results

They are presented in FIG. 4 and FIG. 5.

Figure 4A:
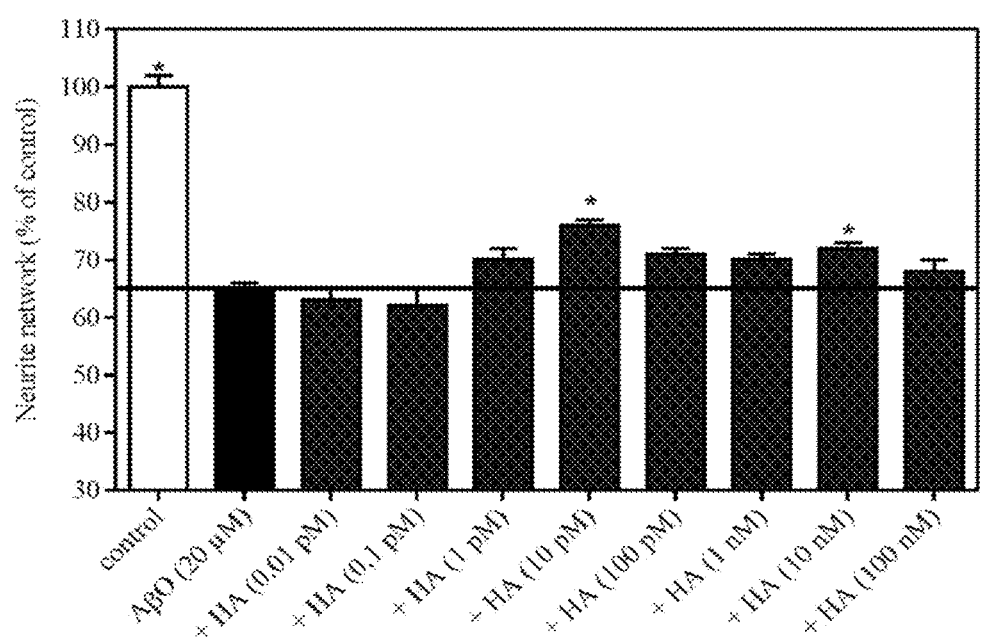
FIG. 4 illustrates the effect of Huperzine A (HA) (a, b), caffeic acid (CA) (c, d) and ferulic acid (FA) (e, f) at different concentrations on the toxicity of Aβ-peptide (20 μM, 24 hours) on neurite network a, c et e) and primary cortical neuron survival (b,d et f). Data were expressed as percentage of control as mean±SEM (100%=no Aβ). * $p<0.05$ vs Aβ (one way ANOVA followed by Dunnett's test).
Figure 4B:
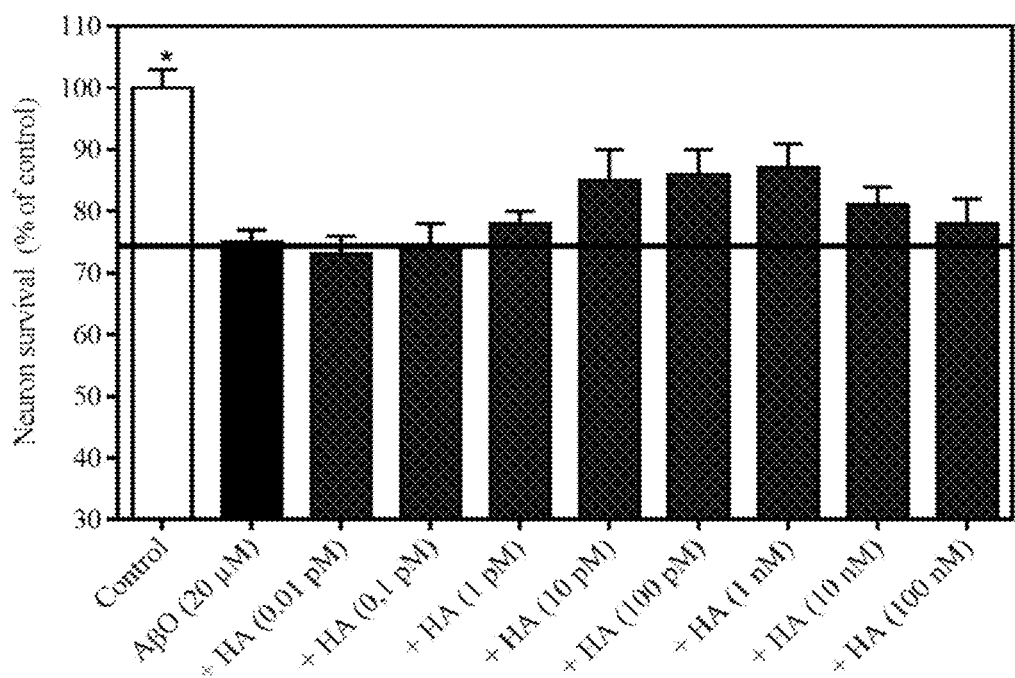
Figure 4C:
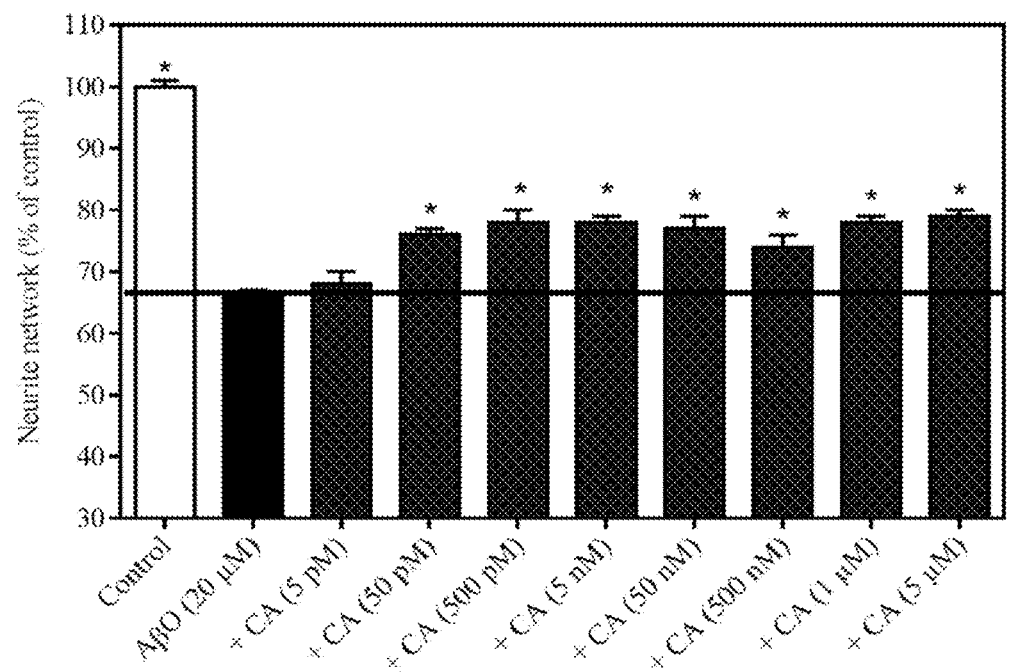
Figure 4D:
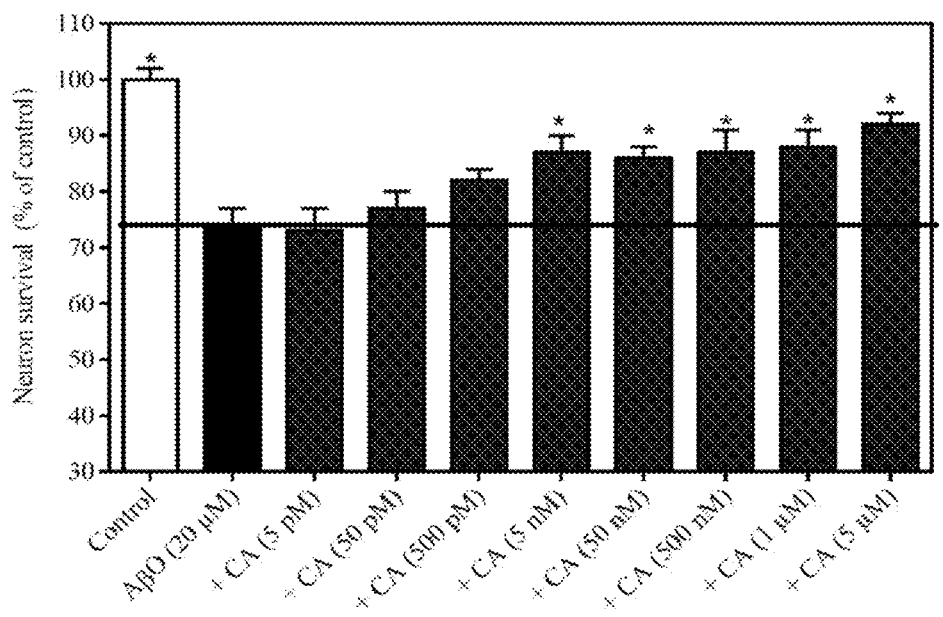
Figure 4E:
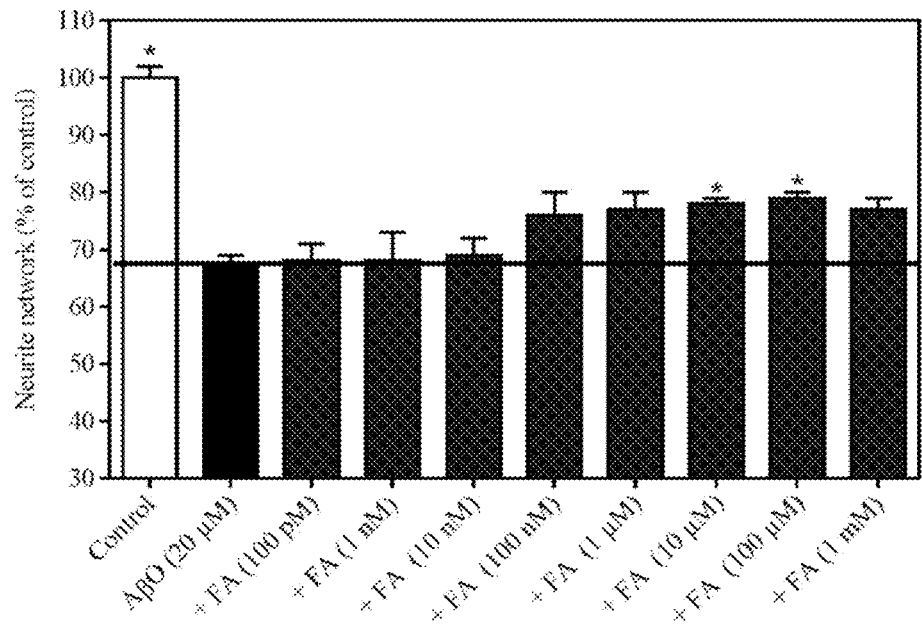
Figure 4F:
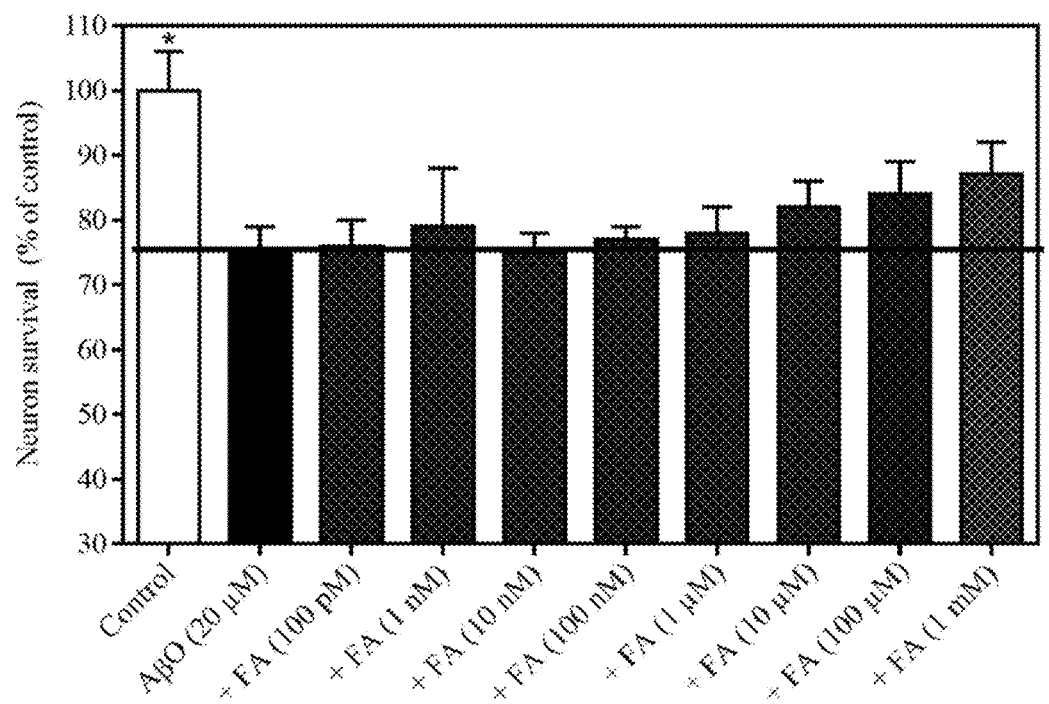

Aβ(20 μM, 24 h) induced a significant neuronal death (~25%) and a large loss of neurite (by 35%).

huperzine A (HA) was not able to significantly protect the neurons from injuries (FIG. 4b). By contrast, HA in a concentration of 10 pM and 10 nM had significant effects on the neurite network (FIG. 4a);

caffeic acid was able to significantly protect the neurons from injuries at concentrations from 5 nM up to 5 μM. At concentrations of 500 pM and below, no effect was observed on neuron survival (FIG. 4d). Protective effect on the neurite network was observed even at lower concentrations (FIG. 4c);

ferulic acid was not able to protect the neurons from injuries whatever the concentration tested (FIG. 4f). A small effect was observed on the neurite network with a significant effect for 10 and 100 μM (FIG. 4e).

The effect of mixtures of HA, CA and FA on primary cortical neurons injured by Aβ are given in FIG. 5. Such combinations according to the invention strongly protect neurons from Aβ-toxicity under experimental conditions described above.

Aβ (20 μM, 24 h) induced a significant neuronal death (~25%) and a large loss of neurite (by 40%).

Figure 5A:
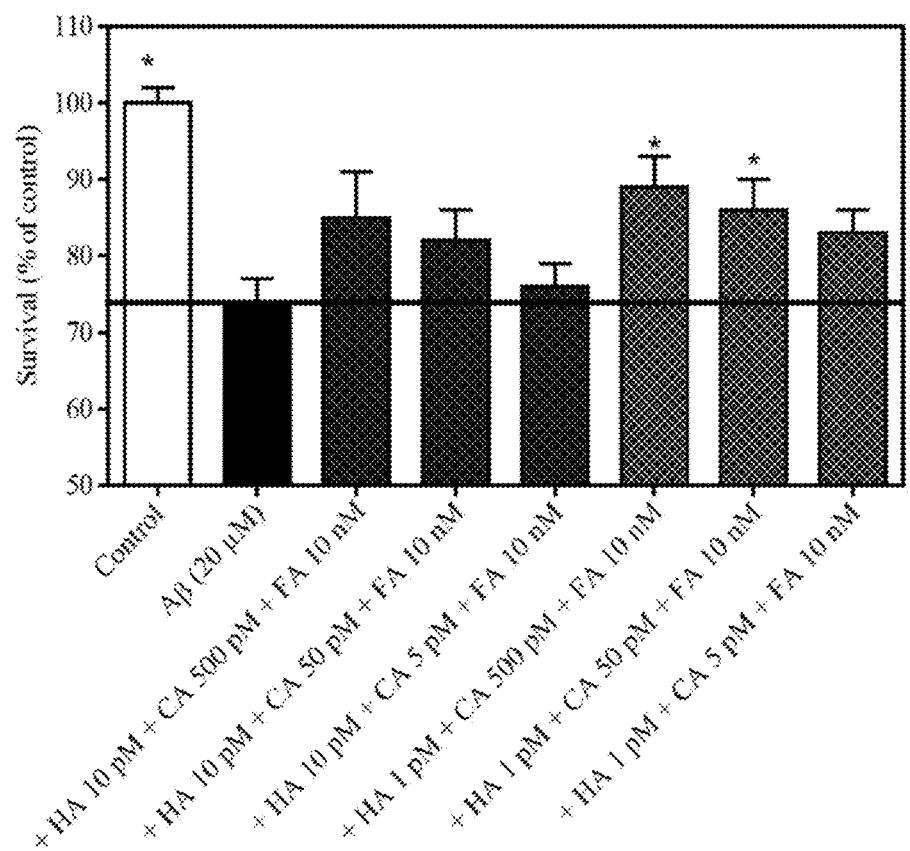
FIG. 5 illustrates the effect of mixtures of huperzine A (HA), caffeic acid (CA) and ferulic acid (FA) at different ratios on the toxicity of Aβ-peptide (20 μM, 24 hours) on primary cortical neuron survival (a) and neurite network (b). Data were expressed as percentage of control as mean±SEM (100%=no Aβ). * $p<0.05$ vs Aβ (one way ANOVA followed by PLSD Fisher's test).
Figure 5B:
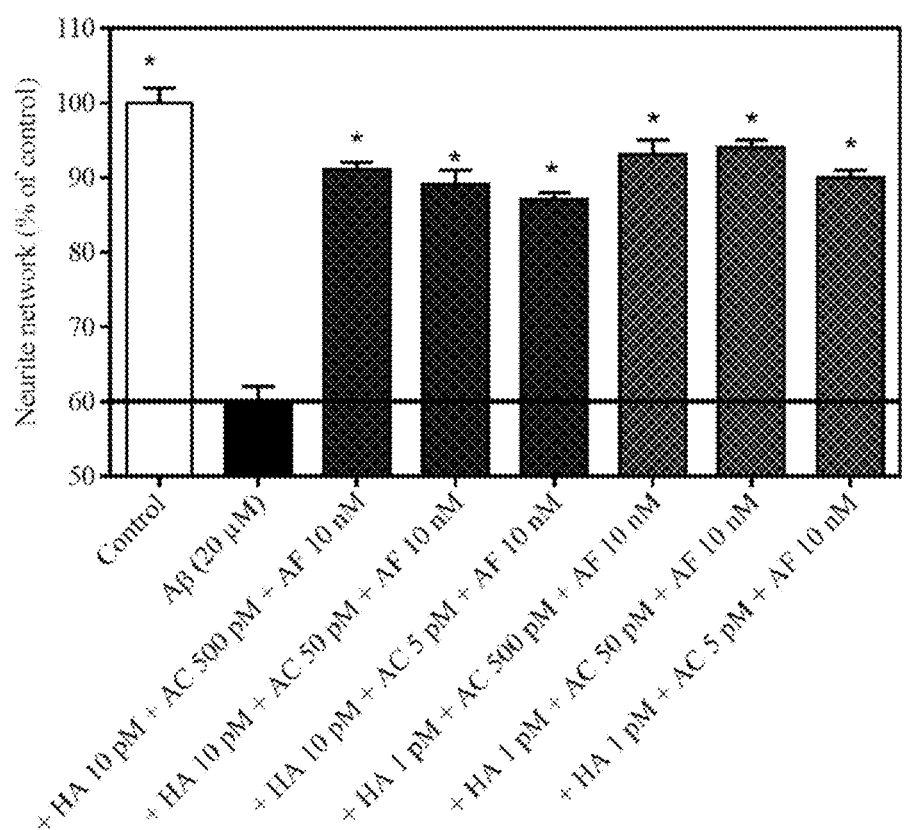

In presence of a mixture of HA/CA/FA a significant protective effect was observed (~90% of survival) on the neuron survival and all the tested concentrations showed a protective effect. The following mixture concentrations resulted in a significant increase of cortical neuron survival: 1 pM/500 pM/10 nM (HA/CA/FA); 1 pM/50 pM/10 nM (HA/CA/FA) respectively (FIG. 5a). Most importantly, all the concentration combinations of the three compounds displayed a significant protective effect on the neurite network, preserving it almost completely. All tested mixtures protected to more than 90% from Aβ-induced neurite loss (FIG. 5b).

It has to be reminded that at the concentrations used, none of the three compounds used alone was able to display any protective effect (FIG. 4).

This study proved that huperzine A, caffeic acid and ferulic acid were able to protect neurons from injuries induced both by glutamate and β-amyloid peptide. More interesting and surprisingly, we showed in this study that huperzine A, caffeic acid and ferulic acid, when used in combination at concentrations where the individual components are ineffective, were able to provide almost complete neuroprotection in both glutamate- and β-amyloid-injuries.

For the first time a synergistic neuroprotective effect of the mixture of these compounds was clearly shown. Thus, the present invention advantageously provides compositions containing low concentrations of huperzine A, therefore allowing for reducing unpleasant side-effects usually produced by alkaloid drugs such as sweating, nausea, vomiting, dizziness, and cramps [Yang G. et al., PLOS ONE (2013), 8(9): e74916].

Same results have been obtained with all extracts whatever the method of extraction except for the extract N6002-5 (in which FA was not present).

EXAMPLE 4: PREVENTION OF MPP TOXICITY ON NEURONAL CELLS

Additional investigations were done in light of these previous results to test the putative efficacy of NSP01-001-E001 (batch: a) on Tyrosine hydroxylase (TH) positive neurons injured with (1-methyl-4-phenylpyridinium (MPP$^+$) which is a well validated model of Parkinson disease (PD). [Visanji N P, et al. FASEB J. 2008; 22(7):2488-97].

1. Experimental Section
   a. Plant Extract NSP01-001-E001

*Huperzia serrata* (HS) extract NSP01-001-E001 was obtained by extraction such as decoction (pH 7; 30 min). The extract contains a ratio of 1/0.1/0.6 of HA/CA/FA.

b. Culture of Mesencephalic Neurons

The neuroprotective effect of HS extract was assessed by quantification of the TH positive neurons which specifically reveals the dopaminergic neuron survival. Rat dopaminergic neurons were cultured as described by Schinelli et al., J Neurochem. 1988 June; 50(6):1900-7 and Visanji et al., 2008 [previously cited].

Briefly, the midbrains obtained from 15-days old rat embryos (Janvier Labs, France) were dissected under a microscope. The embryonic midbrains were removed and placed in ice-cold medium of Leibovitz (L15, Pan Biotech) containing 2% of Penicillin-Streptomycin (PS, Pan Biotech) and 1% of bovine serum albumin (BSA, Pan Biotech). The ventral portion of the mesencephalic flexure, a region of the developing brain rich in dopaminergic neurons, was used for the cell preparations.

The midbrains were dissociated by trypsinisation for 20 min at 37° C. (Trypsin 0.05% EDTA 0.02%, PanBiotech). The reaction was stopped by the addition of Dulbecco's modified Eagle's medium (DMEM, PanBiotech) containing DNAase I grade II (0.1 mg/ml, PanBiotech) and 10% of foetal calf serum (FCS, Gibco). Cells were then mechanically dissociated by 3 passages through a 10 ml pipette. Cells were then centrifuged at 180×g for 10 min at +4° C. on a layer of BSA (3.5%) in L15 medium. The supernatant was discarded and the cell pellets were re-suspended in a defined culture medium consisting of Neurobasal (Invitrogen) supplemented with B27 (2%, Invitrogen, Batch: 1589889), L-glutamine (2 mM, PanBiotech) and 2% of PS solution and 10 ng/ml of Brain-derived neurotrophic factor (BDNF, PanBiotech) and 1 ng/ml of Glial-Derived Neurotrophic Factor (GDNF, PanBiotech). Viable cells were counted in a Neubauer cytometer using the trypan blue exclusion test. The cells were seeded at a density of 40 000 cells/well in 96 well-plates pre-coated with poly-L-lysine (Corning Biocoat) and maintained in a humidified incubator at 37° C. in 5% $CO_2$/95% air atmosphere. Half of the medium was changed every 2 days with fresh medium.

On day 6 of culture, the medium was removed and fresh medium was added, without or with MPP$^+$ (Sigma) at 4 µM diluted in control medium, 6 wells per condition were assessed.

c. Tests Compounds and MPP$^+$ Exposure

On day 6 of culture, NSP01-001-E001 (2.5, 5, 50, 500 ng/ml, 2.5, 5, 25, 33.3 µg/ml) were solved or diluted in culture medium and then pre-incubated with primary mesencephalic neurons for 1 hour before the MPP$^+$ application. MPP$^+$ solution was added to a final concentration of 4 µM diluted in control medium.

d. TH Positive Neurons Assessment

After 48 hours intoxication, the cells were then fixed by a solution of 4% paraformaldehyde (PFA, Sigma) in PBS (PAN), pH=7.3 for 20 min at room temperature. The cells were washed again twice in PBS, and then were permeabilized and non-specific sites were blocked with a solution of PBS containing 0.1% of saponin (Sigma) and 1% FCS for 15 min at room temperature. Then, cells were incubated with Monoclonal Anti-Tyrosine Hydroxylase (TH, Sigma) antibody produced in mouse at dilution of 1/10000 in PBS containing 1% FCS, 0.1% saponin, for 2 h at room temperature. This antibody was revealed with Alexa Fluor 488 goat anti-mouse IgG (Molecular probe) at the dilution 1/800 in PBS containing 1% FCS, 0.1% saponin, for 1 h at room temperature.

The immunolabeled cultures were automatically examined with ImageXpress (Molecular Devices) equipped with a LED at ×10 magnification. For each condition (6 culture wells), 20 automatically fields per well (representing ~80% of the total surface of the well) were analyzed. The total number of TH neurons was automatically analyzed using MetaXpress software (Molecular Devices). Data were expressed in percentage of control conditions (no intoxication, no MPP$^+$=100%) in order to express the MPP$^+$ injury. All values were expressed as mean±SEM (s.e. mean) of the 6 wells. Graphs and statistical analyses were performed on the different conditions (ANOVA followed by Dunnett's or PLSD Fisher's test when allowed, using GraphPad Prism software).

2. Results

They are shown in FIG. 6.

MPP$^+$ (4 µM-48 h) induced a significant cell death (>35%) as previously shown in literature [Visanji et al., 2008 previously cited]. As shown in FIG. 6, in presence of NSP01-001-E001 (from 50 ng/ml up to 5 µg/ml), a large and significant protective effect on the TH positive neurons was observed (>90% of survival for 2.5 and 5 µg/ml dose).

A bell shape curve was observed. At the highest concentration (25 and 33.3 µg/ml), NSP01-001-E001 did not show any protective effect. The 2 lowest test doses (2.5 and 5 ng/ml) were inactive.

They demonstrate that NSP01-001-E001 was able to protect neuron from MPP$^+$ injuries (a well validated model of PD) and that NSP01-001-E001 contained a specific ratio of 3 essential components (HA/CA/FA) which were proven in previous investigations to be at the origin of the neuroprotective activity.

EXAMPLE 5: PREVENTION OF MPP$^+$ TOXICITY ON NEURONAL CELLS BY HUPERZINE A, CAFFEIC ACID, AND FERULIC ACID

In view of the results obtained with NSP01E01 (batches N6001-6 and N6002-6, *Huperzia serrata*) which show that said extracts protected cortical neurons and neurites from glutamate injuries and following analysis of the chemical profile, Huperzine A, (HA), Caffeic acid (CA) and Ferulic acid (FA) were suspected to be involved in this effect and were tested on Tyrosine hydroxylase (TH) positive neurons injured with (1-methyl-4-phenylpyridinium (MPP$^+$) which is a well validated model of Parkinson disease (PD) according to example 4.

1. Experimental Section

The protocol used in these assays is the same as described in example 4. On day 6 of culture, test compounds (HA, CA and FA) were solved and diluted in culture medium and then pre-incubated with mesencephalic neurons for 1 hour before the MPP$^+$ application.

HA (1, 10, 100 nM, 1, 10, 100 µM), CA (5, 50, 500 pM, 5, 50, 500 nM, 1 µM), FA (100 pM, 1, 10, 100 nM, 1, 10, 100 µM and 1 mM) and mixtures thereof were solved or diluted in culture medium and then pre-incubated with primary mesencephalic neurons for 1 hour before the MPP$^+$ application. MPP$^+$ solution was added to a final concentration of 4 µM diluted in control medium.

After 48 hours of intoxication, the cells were then fixed and the number of TH positive neurons were assessed as described in example 4.

2. Results

They are shown in FIGS. 7a-d.

Figure 7A:
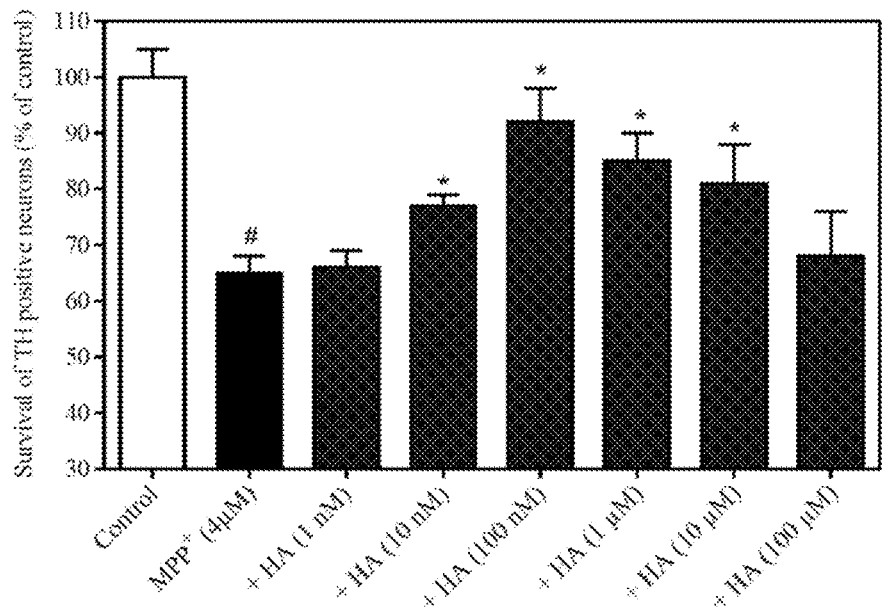

FIG. 7a shows that MPP$^+$ (4 µM-48 h) induced a significant cell death (>35%) as previously shown in literature [Visanji et al., 2008, previously cited]. In presence of HA (from 10 nM up to 10 µM), a large and significant protective effect was observed (>90% of survival for 100 nM concentration).

A bell shape curve was observed. At the highest concentration (100 µM), HA did not show some protective effect (in some well toxicity occurred). Whereas the lowest test dose (1 nM) was inactive (FIG. 7a).

Figure 7B:
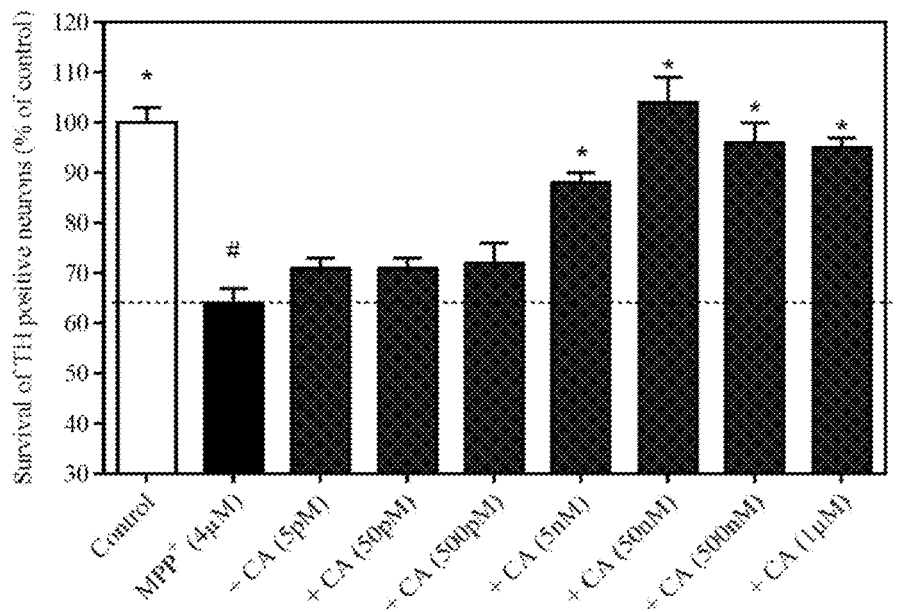

FIG. 7b shows that MPP$^+$ (4 µM-48 h) induced a significant cell death (>35%) as previously shown in literature [Visanji et al., 2008, previously cited]. In presence of CA (5 nM up to 1 µM), a large and significant protective effect was observed.

Figure 7C:
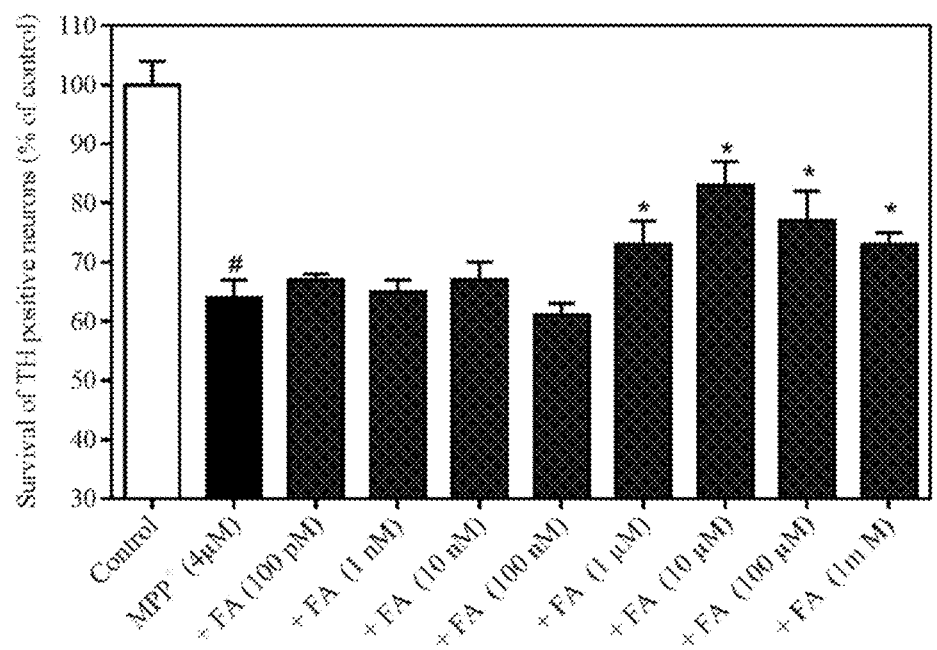

FIG. 7c shows that MPP$^+$ (4 µM-48 h) induced a significant cell death (>35%) as previously shown in literature [Visanji et al., 2008, previously cited]. In presence of FA (from 1 µM to 1 mM), a significant protective effect was observed. Low concentrations were inactive (100 pM up to 100 nM), the effect following a bell shape curve with maximal effect for 10 µM.

Figure 7D:
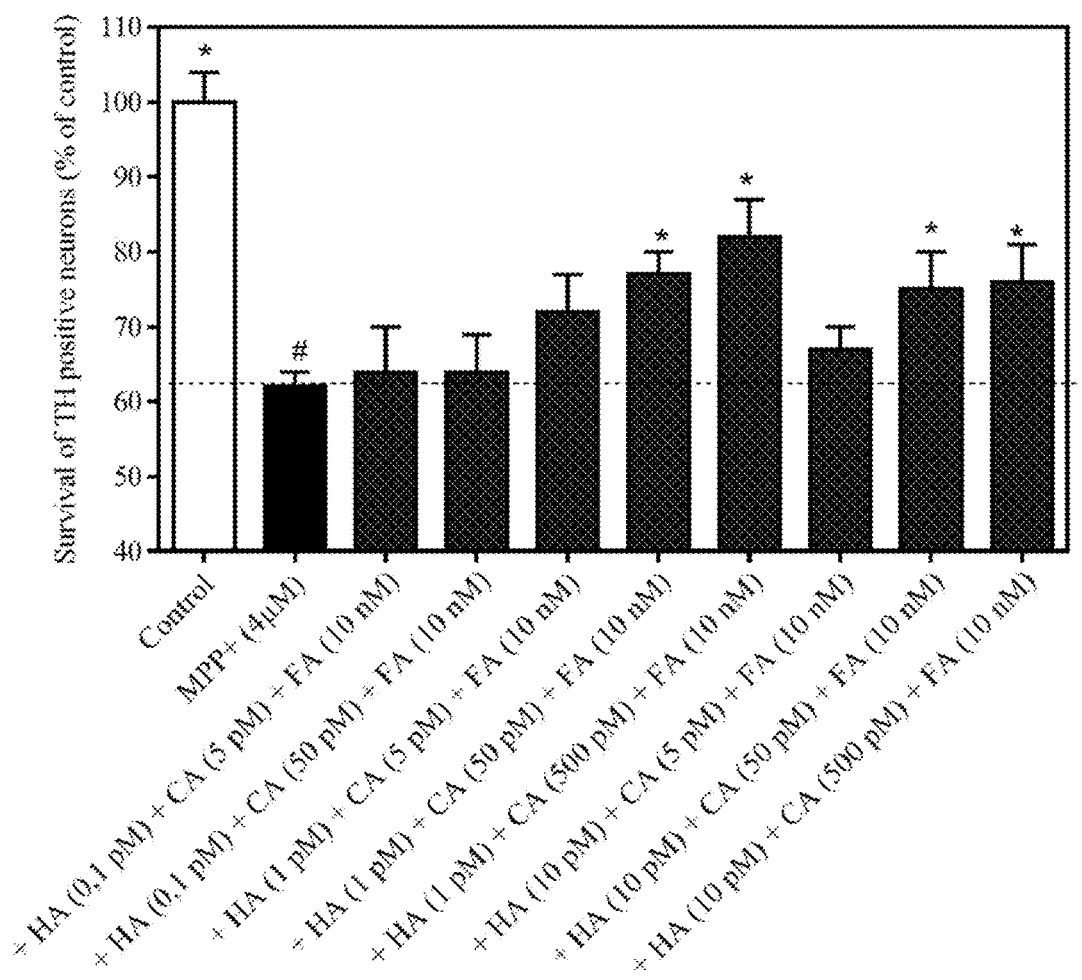

FIG. 7d shows that MPP$^+$ (4 µM-48 h) induced a significant cell death (>35%) as previously shown in literature [Visanji et al., 2008, previously cited]. In presence of a mixture of HA/CA/FA added 1 h before MPP$^+$ and let during the MPP$^+$ application for 48 h, a significant protective effect was observed (~82% of survival for the HA/CA/FA: 1 pM/500 pM/10 nM) on the neuron survival. All the tested mixtures, whatever the concentrations of HA, CA or FA in the mixture showed a protective effect, and a significant effect for the following mixtures HA/CA/FA: 1 pM/50 pM/10 nM; 1 pM/500 pM/10 nM; 10 pM/50 pM/10 nM and 10 pM/500 pM/10 nM, whereas at said concentrations the compounds alone were inactive.

EXAMPLE 6: PREVENTION OF GLUTAMATE TOXICITY ON NEURONAL CELLS BY HUPERZINE A, CAFFEIC ACID, SINAPIC ACID, FERULIC ACID, P-COUMARIC ACID AND GALLIC ACID

In this study, the synergistic effect of HA combined with other polyphenol such as Sinapic acid (SA), para-coumaric acid (pCouA), galic acid (GA), Ferulic acid (FA) or Caffeic acid (CA) was assessed on cortical neurons injured with glutamate a well validated in vitro model of Alzheimer Disease (AD) [Campos-Peña et al. (2014). Alzheimer Disease: The Role of Aβ in the Glutamatergic System, Neurochemistry, Dr. Thomas Heinbockel (Ed.), ISBN: 978-953-51-1237-2, InTech, DOI: 10.5772/57367].

1. Experimental Section

Rat cortical neurons were cultured as in example 1.

Neurons were intoxicated with glutamate solutions (see below) after 13 days of culture.

On day 13, glutamate (Sigma Aldrich, Lyon, France, Batch: SLBL7326V) was added into cell culture to a final concentration of 40 µM diluted in control medium in presence or absence of test compounds for 20 min.

After 20 min, the cells were washed-out and new fresh medium containing or not test compounds was added for 48 h additional time.

On day 13 of culture, test compounds (HA, CA, SA, GA, p-CouA and FA) were solved in DMSO and diluted in culture medium and then pre-incubated with cortical neurons 1 hour before the glutamate application.

HA (10 pM) (non-active concentration, see example 2), CA (500 pM, non-active concentration, see example 2), FA (10 nM, non-active concentration, see example 2), SA (10, 100 pM, 1, 10, 100 nM, 1, 10 and 50 µM), GA (10, 100 pM, 1, 10, 100 nM, 1, 10 and 50 µM) and pCouA (10, 100 pM, 1, 10, 100 nM, 1, 10 and 50 µM) or mixture of 3 compounds of those at non active concentrations, were solved and diluted in culture medium and then pre-incubated with primary cortical neurons for 1 hour before the glutamate application. Glutamate was added at 40 µM for 20 min.

After 48 hours of glutamate intoxication, cells were fixed by a cold solution of ethanol (95%, Sigma, Batch: SZBD1470V) and acetic acid (5%, Sigma, Batch: SZBD1760V) for 5 min at −20° C. After permeabilization with 0.1% of saponin (Sigma, Batch: BCBJ8417V), cells were incubated for 2 h with mouse monoclonal antibody anti microtubule-associated-protein 2 (MAP-2; Sigma, Batch: 063M4802) at dilution of 1/400 in PBS (Pan biotech, Batch: 1870415) containing 1% foetal calf serum and 0.1% of saponin.

This antibody was revealed with Alexa Fluor 488 goat anti-mouse IgG (Invitrogen, Batch: 1664729) at the dilution of 1/400 in PBS containing 1% foetal calf serum and 0.1% of saponin for 1 h at room temperature.

Neuron survival and neurite network length assessment: The immunolabeled cultures were automatically examined with ImageXpress (Molecular Devices, USA) equipped with a LED at ×20 magnification. For each condition (6 culture wells), 30 automatically fields per well (representing ~80% of the total surface of the well) were analyzed. The total number of neurons and the total neurite network were automatically analyzed using MetaXpress software (Molecular Devices).

Data were expressed in percentage of control conditions (no intoxication, no glutamate=100%) in order to express the glutamate injury. All values were expressed as mean+/− SEM (s.e.mean) of the 6 wells. Graphs and statistical analyses were performed on the different conditions (ANOVA followed by PLSD Fisher's test when allowed, using Statview and GraphPad Prism software).

2. Results

They are shown in FIG. 8a-d.

Figure 8A:
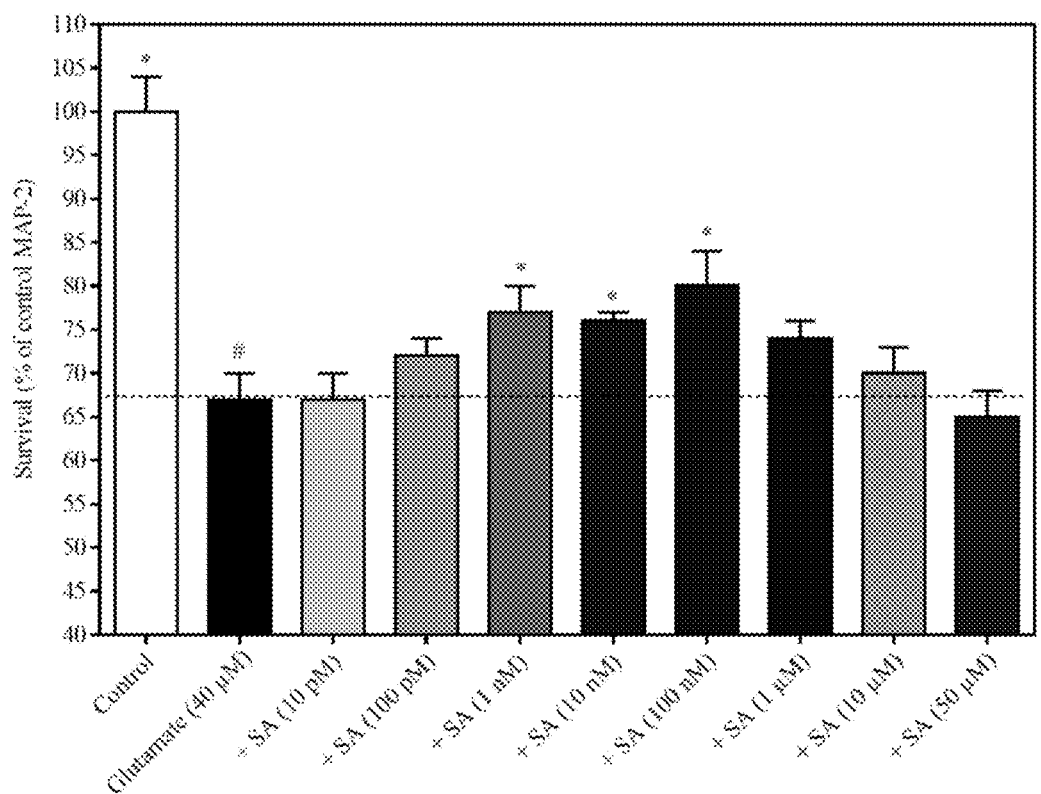
Figure 8B:
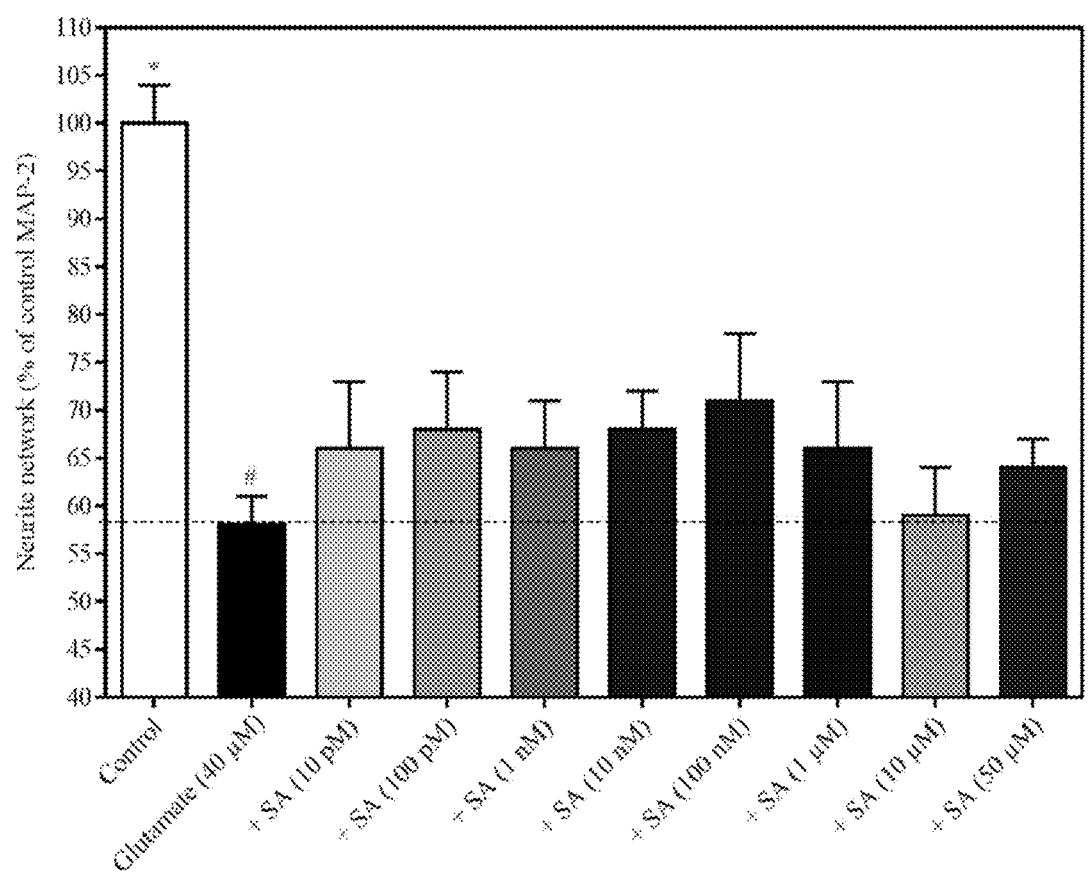

FIG. 8a shows that Glutamate (40 µM, 20 min) induced a significant neuronal death (>30%) and large injuries on neurite network of neurons (>40%). When SA (100, 10 and 1 nM) is added 1 h before the glutamate, let during the toxic application and for the next 48 h after wash-out, a significant protective effect was observed (~80% of survival) on the neuron survival (FIG. 8a). SA was inactive at the lowest concentrations (FIG. 8a). Additionally, no protective effect was observed on the neurite network (FIG. 8b)

Figure 8C:
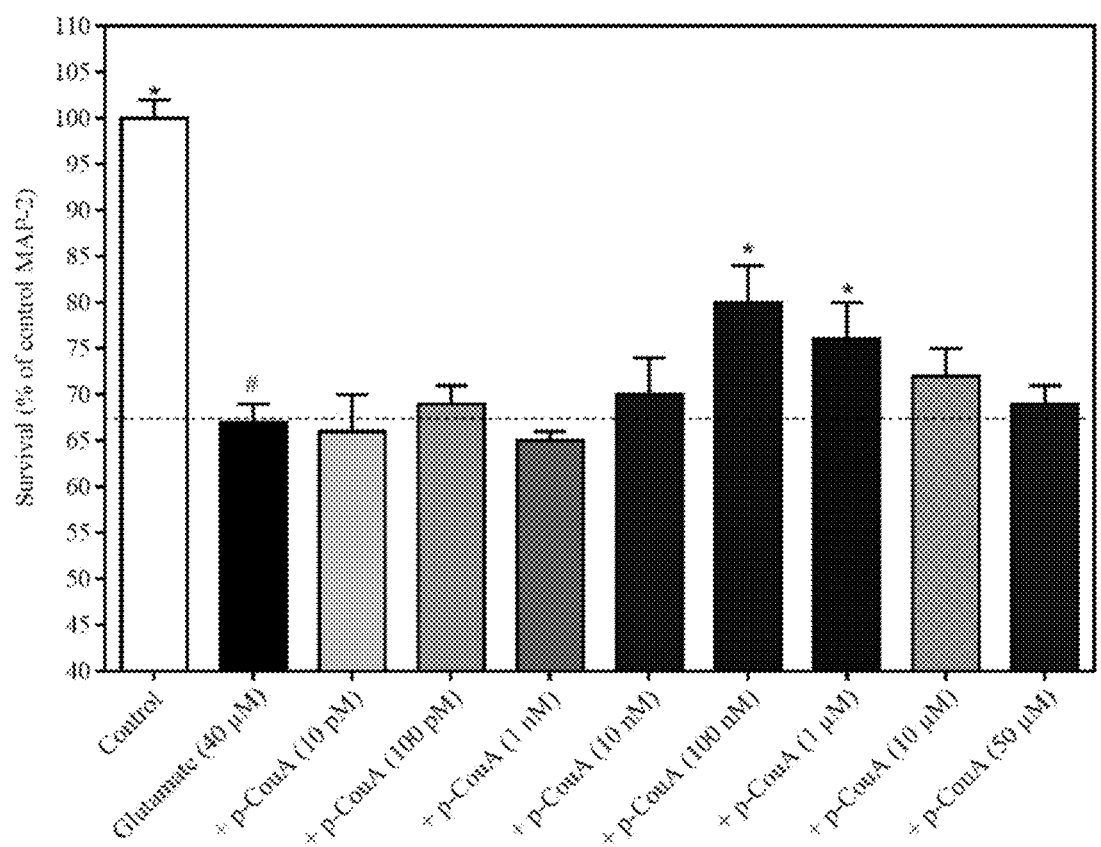
Figure 8D:
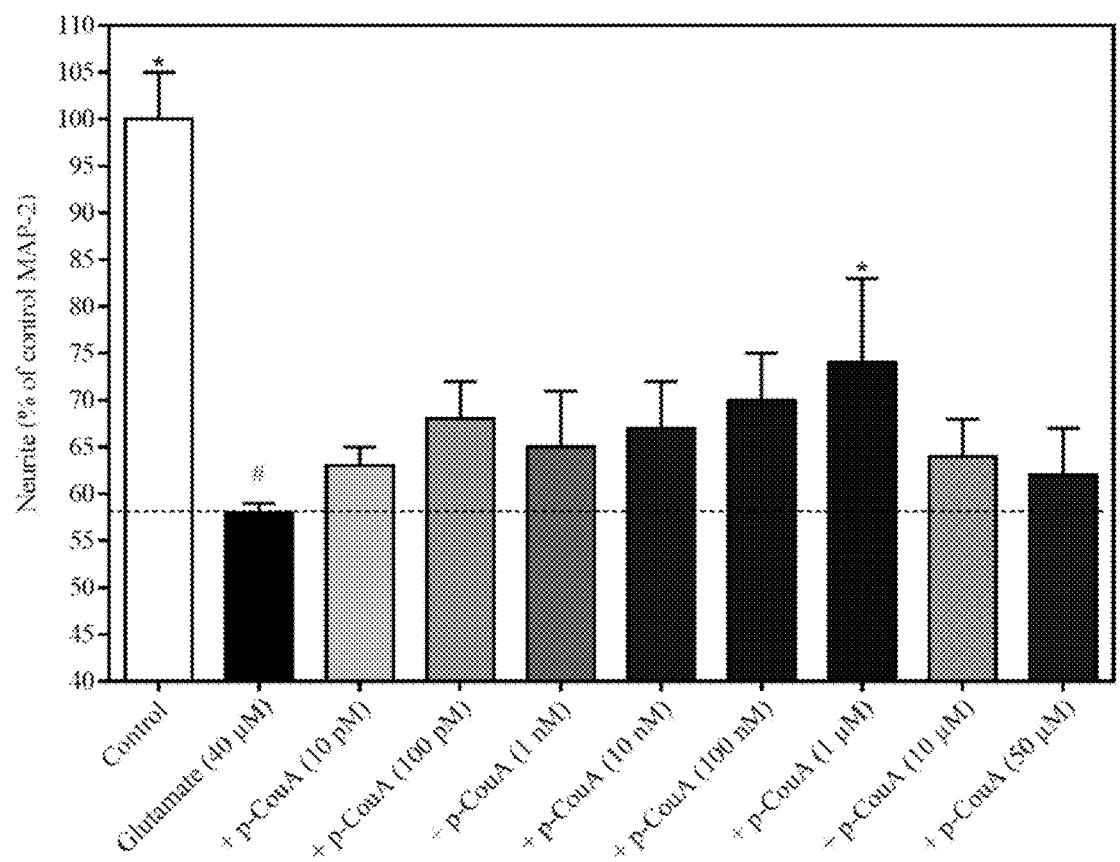

FIG. 8c shows that Glutamate (40 µM, 20 min) induced a significant neuronal death (>30%) and large injuries on neurite network of neurons (>40%). When pCouA (100 nM and 1 µM) is added 1 h before the glutamate and let during the toxic application and as well as the next 48 h after wash-out, a significant protective effect was observed (~80% of survival, FIG. 8c). On the neurite network only 1 µM of p-CouA showed a protective effect (FIG. 8d). It could be mentioned that at the lowest concentrations p-CouA was inactive both on the survival and the neurite network.

Figure 8E:
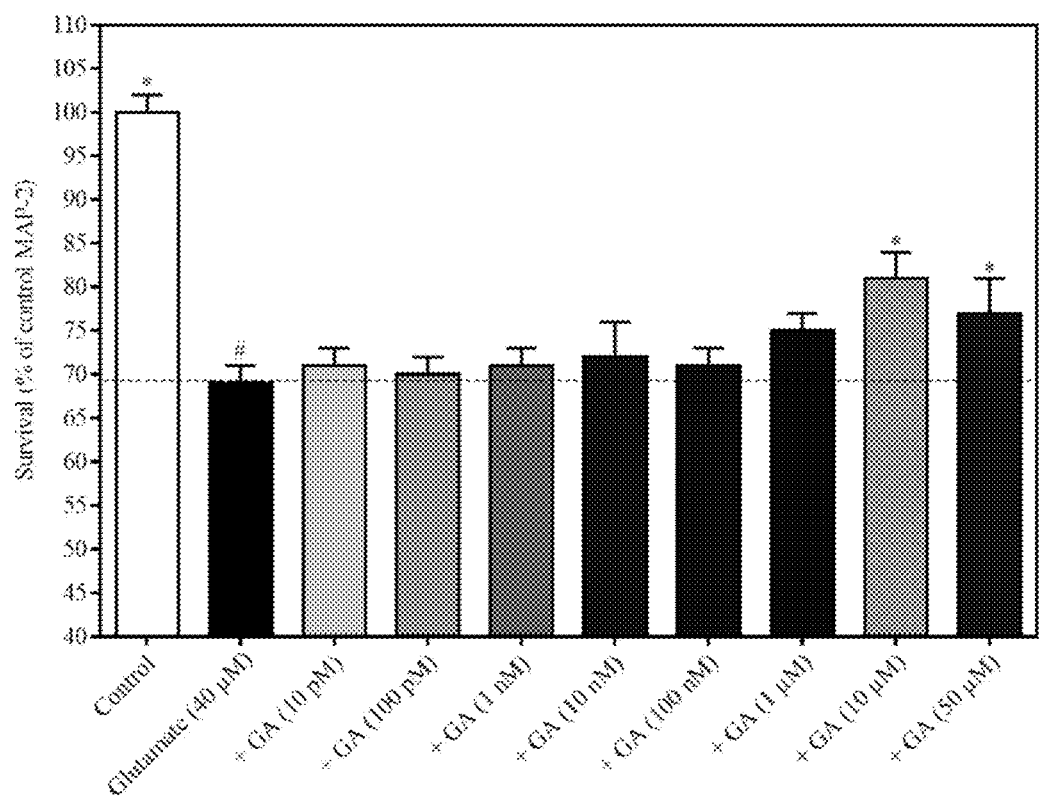
Figure 8F:
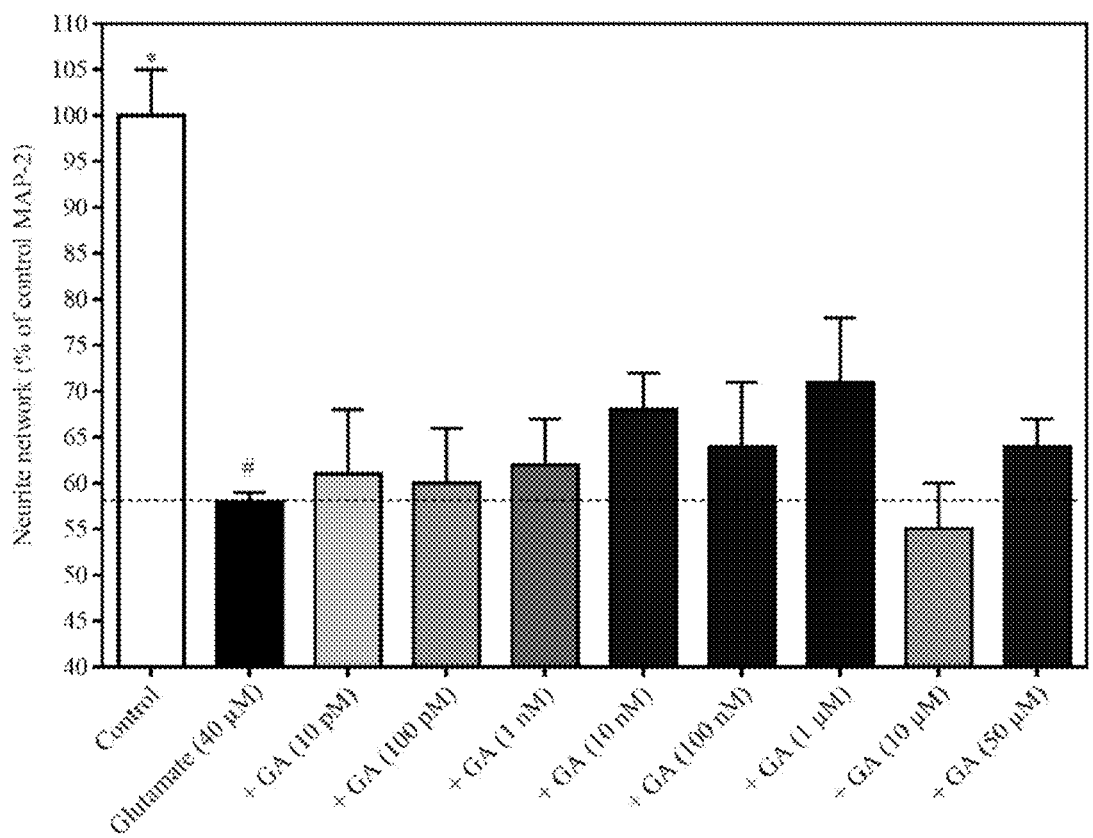

FIG. 8e shows that Glutamate (40 µM, 20 min) induced a significant neuronal death (>30%) and large injuries on neurite network of neurons (>40%). When GA (10 and 50 µM) is added 1 h before the glutamate and let during the toxic application and let for the next 48 h after wash-out, a significant protective effect was observed (~80% of survival) except at the lowest concentrations (up to 1 µM, FIG. 8e). On the neurite network no protection was observed (FIG. 8f).

Figure 8G:
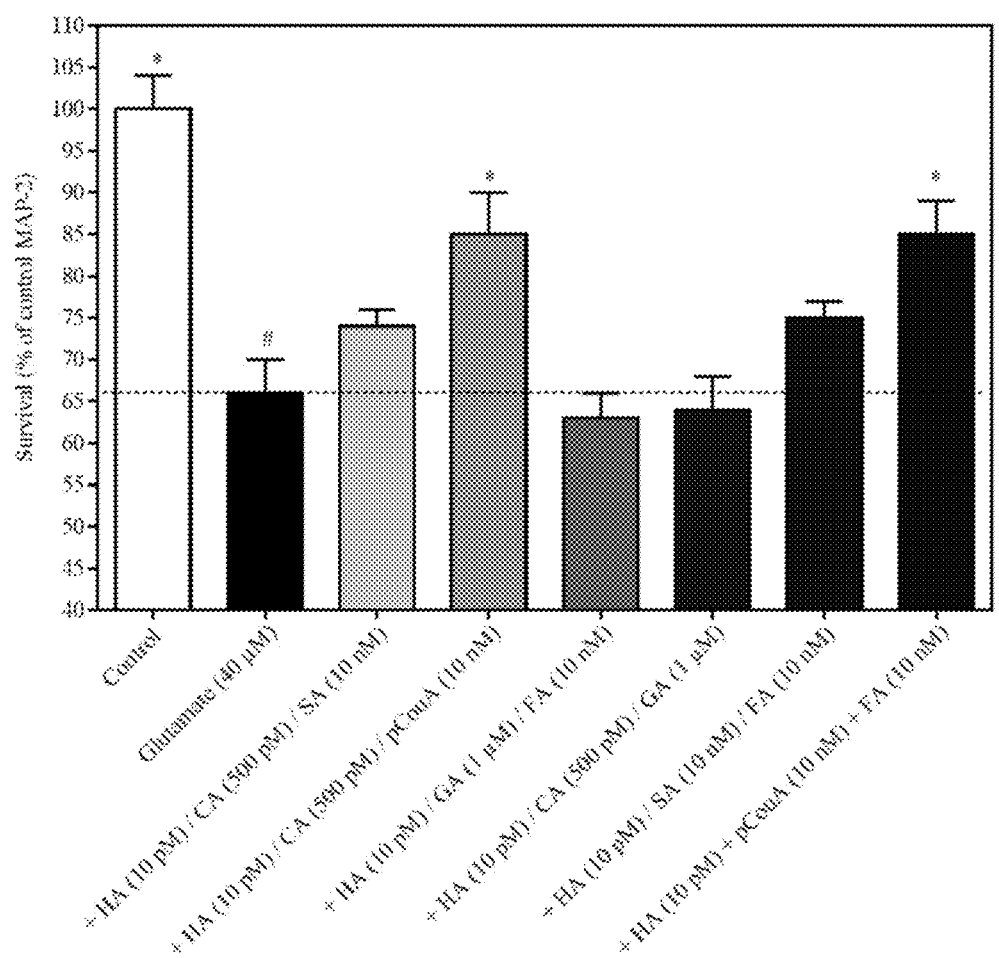
Figure 8H:
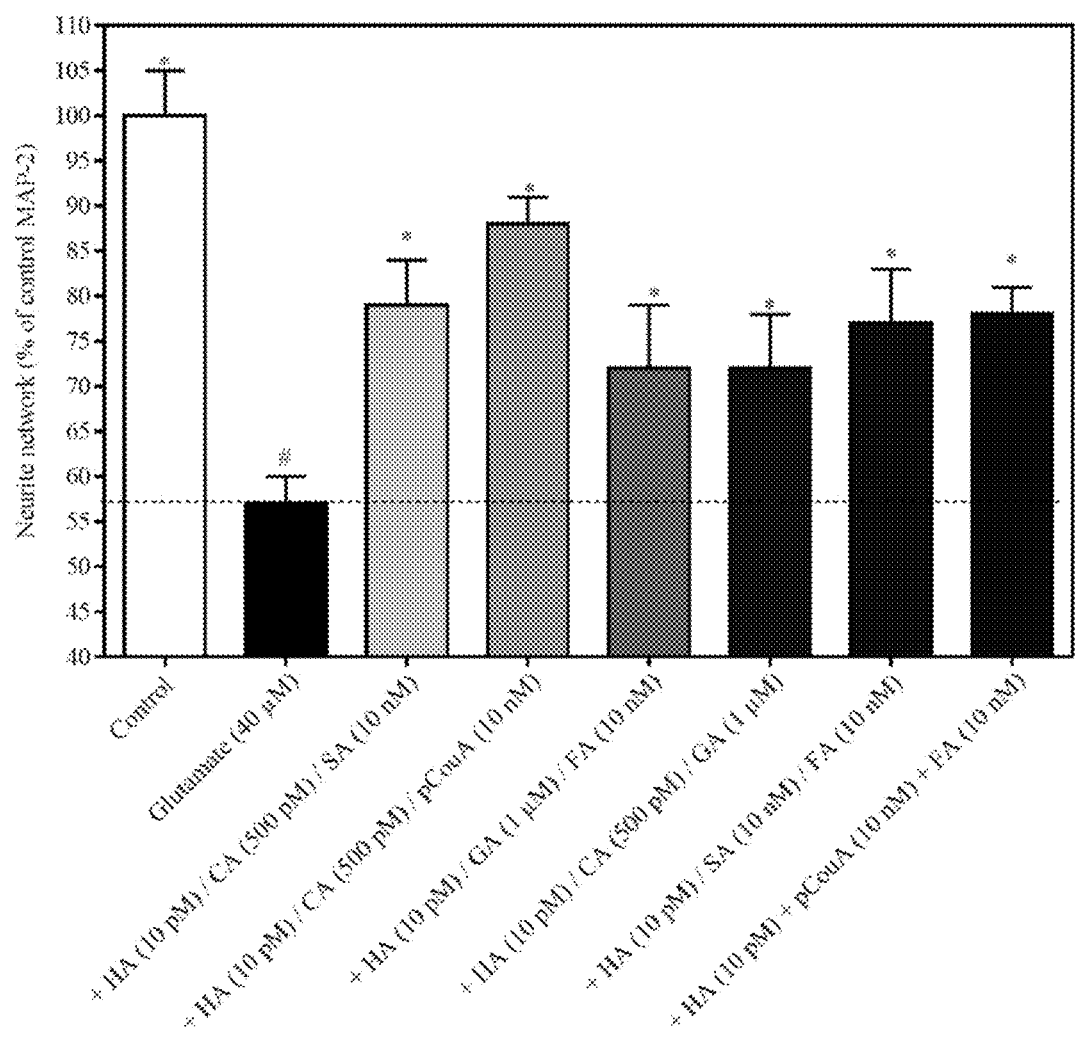

FIG. 8g shows that Glutamate (40 µM, 20 min) induced a significant neuronal death (>30%) and large injuries on neurite network of neurons (>40%). In presence of mixture HA/CA/p-CouA (10 pM/500 pM/10 nM) and HA/p-CouA/FA (10 pM/10 nM/10 nM) added 1 h before the glutamate and let during the toxic application and let for the next 48 h after wash-out, a significant protective effect was observed (>80%) on the neuron survival (FIG. 8g). These mixtures were also protective on the neurite network (FIG. 8h). In addition the mixture of HA/CA/SA (10 pM/500 pM/10 nM), of HA/CA/pCoua (10 pM/500 pM/10 nM), of HA/GA/FA (10 pM/1 µM/10 nM), of HA/CA/GA (10 pM/500 pM/1 µM), of HA/SA/FA (10 pM/10 nM/10 nM) and HA/pCouA/FA (10 pM/10 nM/10 nM) also significantly protected the neurite network (FIG. 8h).

It has to be reminded that at all these concentrations used, none of the 3 compounds were able to display any protective effect when used alone (see Example 2 and FIGS. 2 a-f).

EXAMPLE 7: PREVENTION OF GLUTAMATE TOXICITY ON NERVE/MUSCLE CO-CULTURES BY HUPERZINE A, CAFFEIC ACID, AND FERULIC ACID

In this study the neuroprotective effect of a Huperazine A (HA)/Caffeic Acid (CA)/Ferulic Acid (FA) mixture on nerve/muscle co-culture injured by glutamate exposure, a well validated in vitro ALS model according to Combes et al. [(2015). (J Neurosci Res.; 93(4):633-43)]. The synergic effect of these compounds was also investigated. Evaluation of neuromuscular junction (NMJ) integrity (number and mean size) and neurite network innervating the muscular cells were assessed in presence of the mixture of compounds.

1. Experimental Section

Human muscle (promocell, Batch: 3061107) was prepared according to a previously described method from portions of a biopsy from a healthy subject (Braun et al., (1996) J. Neurol Sci. 136: 17-23). The human muscle cell line was established from dissociated cells (21 000 cells per wells), plated in gelatin-coated 0.1% (Sigma, Batch: 051M0012V) in water on 48 wells plate (greiner, Batch: E13111ME) and grows in a proliferation medium consisting of mix of 62% of MEM medium (PAN, Batch: 2761113) and 25% of M199 medium (PAN, Batch: 6720314) supplemented with glutamine 2 mM (PAN, Batch: 8150713), human insulin 10 µg/ml (PAN, Batch: 1481013), Human recombinant Epidermal growth factor 10 ng/ml (EGF, GIBCO, Batch: 1291552A), human recombinant Fibroblast growth factor basic 2 ng/ml (bFGF, PAN, Batch: H080113), foetal calf serum 10% (FCS, GIBCO, Batch: 41Q7218K) and 2% of Penicillin 10.000 U/ml and Streptomycin 10.000 µg/ml (PS, PAN, Batch: 1451013). The medium was changed every 2 days. Five days after the start of culture, immediately after satellite cell fusion, whole transverse slices of 13-day-old rat Wistar embryos (Janvier, France) spinal cords with 4 dorsal root ganglia (DRG) attached are placed on the muscle monolayer (one explant per well in the central area). DRG are necessary to achieve a good ratio of innervation. Innervated cultures were maintained in a mixed (67%/25%) medium composed of MEM and medium 199, supplemented with 5% FCS, insulin 5 µg/ml, glutamine 2 mM and 2% PS. After 24 h of co-culture, neurites were observed growing out of the spinal cord explants. These neurites made contacts with myotubes and induced the first contractions after ~8 days. Quickly thereafter, innervated muscle fibres located in the proximity to the spinal cord explants, were virtually continuously contracting. Innervated fibres were morphologically and spatially distinct from the non-innervated ones and could easily be distinguished from them.

On day 27, co-cultures were pre-incubated 1 hour before glutamate application with test compounds (different concentrations) tested alone or in a mixture of the 3 compounds.

One hour after HA, CA or FA Compounds and mixture (HA/CA/FA) incubation, glutamate was added to a final concentration of 60 µM diluted in control medium still in presence of 3 compounds or mix of compounds for 20 min.

After 20 min injuries, co-cultures were washed and individual test compounds and mixture were added for an additional 48 h.

After 48 h, the cocultures were prepared for end points evaluation (see below).

After 48H of intoxication, cells were incubated with 500 nM α-bungarotoxin coupled with Alexa 488 (Molecular probes, Batch: 1434893) during 15 min in culture innervations medium at 37° C. to detect NMJ. After 2 washing in PBS (Pan Biotech, Batch: 7560414), cells were fixed by a solution of 4% of paraformaldehyde (Sigma Aldrich, Batch: SLBF7274V) in PBS, pH=7.3 for 20 min at room temperature.

The cells were washed 2 times in PBS and then permeabilized and non-specific sites were blocked with a solution of PBS containing 0.1% of saponin (Sigma-Aldrich, Batch: BCBJ8417V) and 1%0 FCS (Gibco, Batch: 41F0423K) for 15 min at room temperature, co-cultures were incubated with a mouse monoclonal anti-neurofilament 200 KD antibody (NF, Sigma Aldrich, Batch: 053M4756) at the dilution of 1/400 in PBS containing 1% FCS, 0.1% saponin, for 2 h at room temperature. Antibody against NF stained the axon of motor neuron. These antibodies were revealed with Alexa Fluor 568 goat anti-mouse IgG (Invitrogen, Batch: 1218263) at the dilution 1/400 in PBS containing 1% FCS, 0.1% saponin, for 1 h at room temperature. Nuclei of neurons were labeled by Hoechst solution, a nuclear fluorescent marker at 1 µm/ml in the same solution (Hoechst solution, SIGMA, batch: 011M4004V).

The NMJ mean size (area) of NMJs and the total length of neurite were assessed under the experimental conditions described above (see Combes et al., 2015). For each condition, 20 pictures per well were taken in the center area using ImageXpress (Molecular device) with 10× magnification. All images were taken under the same conditions.

The following endpoints were automatically evaluated:

NMJ area: the mean size of the NMJs was measured to assess the quality of innervation.

Neurite length: the length of neurites was measured to assess the extent of the neurite network in the co-culture.

Data were expressed in percentage of control conditions (no induced injury, no glutamate=100%) in order to express the glutamate injury.

All values were expressed as mean+/−SEM (s.e.mean) (n=6 wells per condition per culture). Graphs and statistical analyses were performed on the different conditions (ANOVA followed by PLSD Fisher's test when allowed, using Prism stat software version 5.0).

2. Results

They are shown in FIGS. 9 and 10.

FIGS. 9 a-d show that glutamate (60 µM-20 min) induced a significant NMJ mean size decrease as previously shown in literature [Combes et al., 2015—previously cited].

Figure 9A:
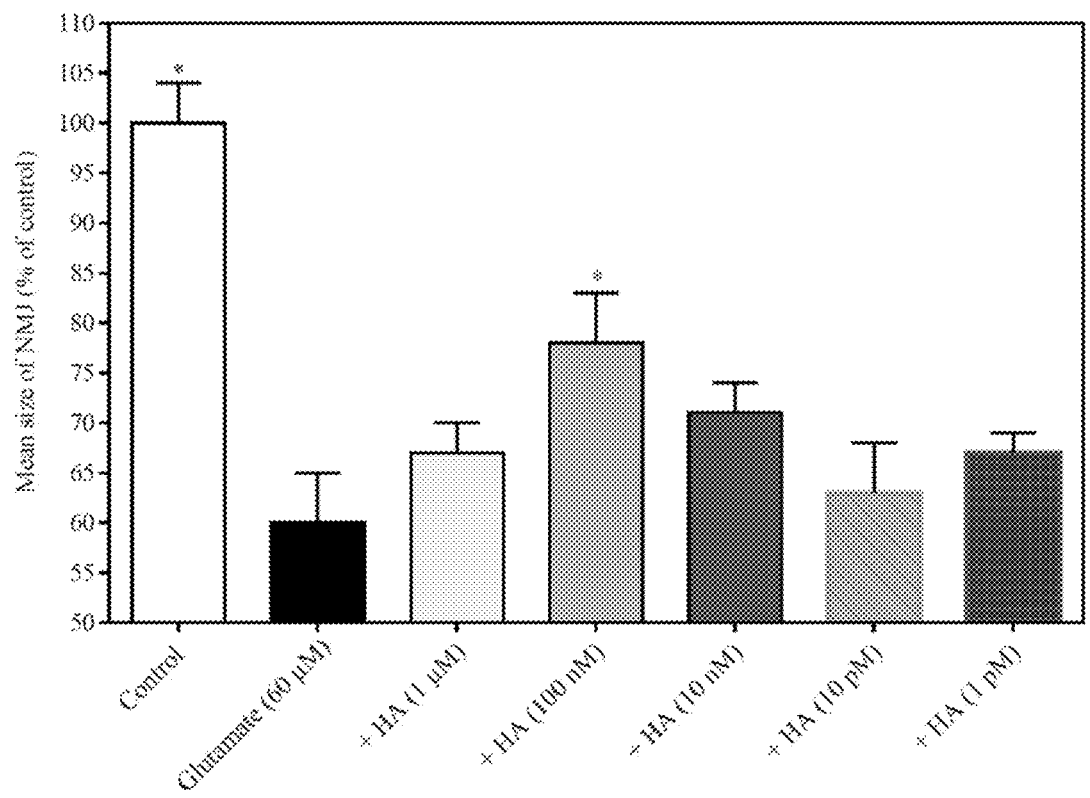

When HA is added (all concentrations tested), a slight protective effect was observed, the significance was observed for 100 nM (FIG. 9a). A bell shape curve effect was observed with HA.

Figure 9B:
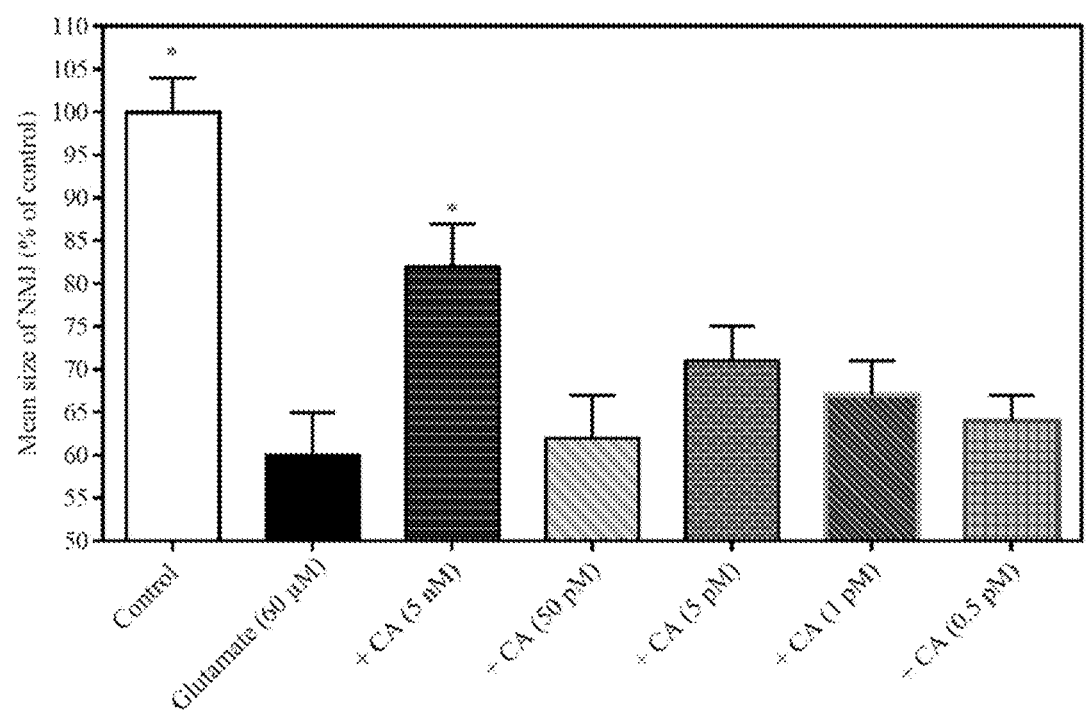

When CA is added 1 h before glutamate it was able to protect NMJs only at the highest dose (5 nM), the low concentrations were unable to protect NMJs from injuries (FIG. 9b).

Figure 9C:
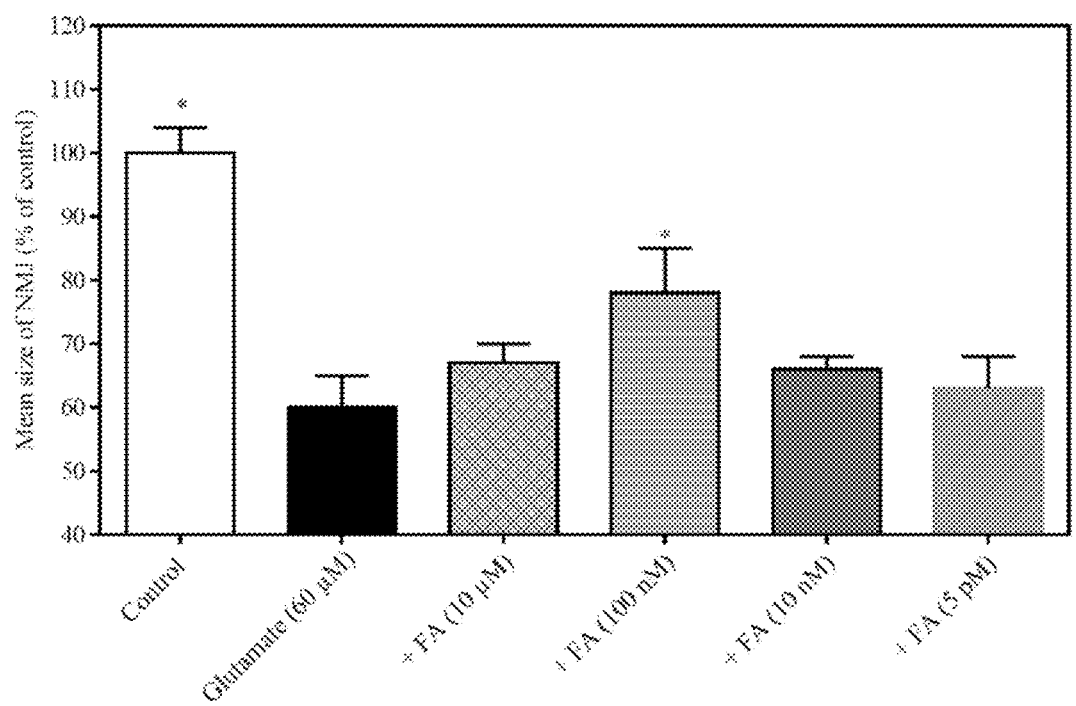

Similarly to HA, FA was able to protect the integrity of NMJs but only at 100 nM (FIG. 9c). A bell shape curve effect was observed (the lowest and the highest concentrations were inactive).

Figure 9D:
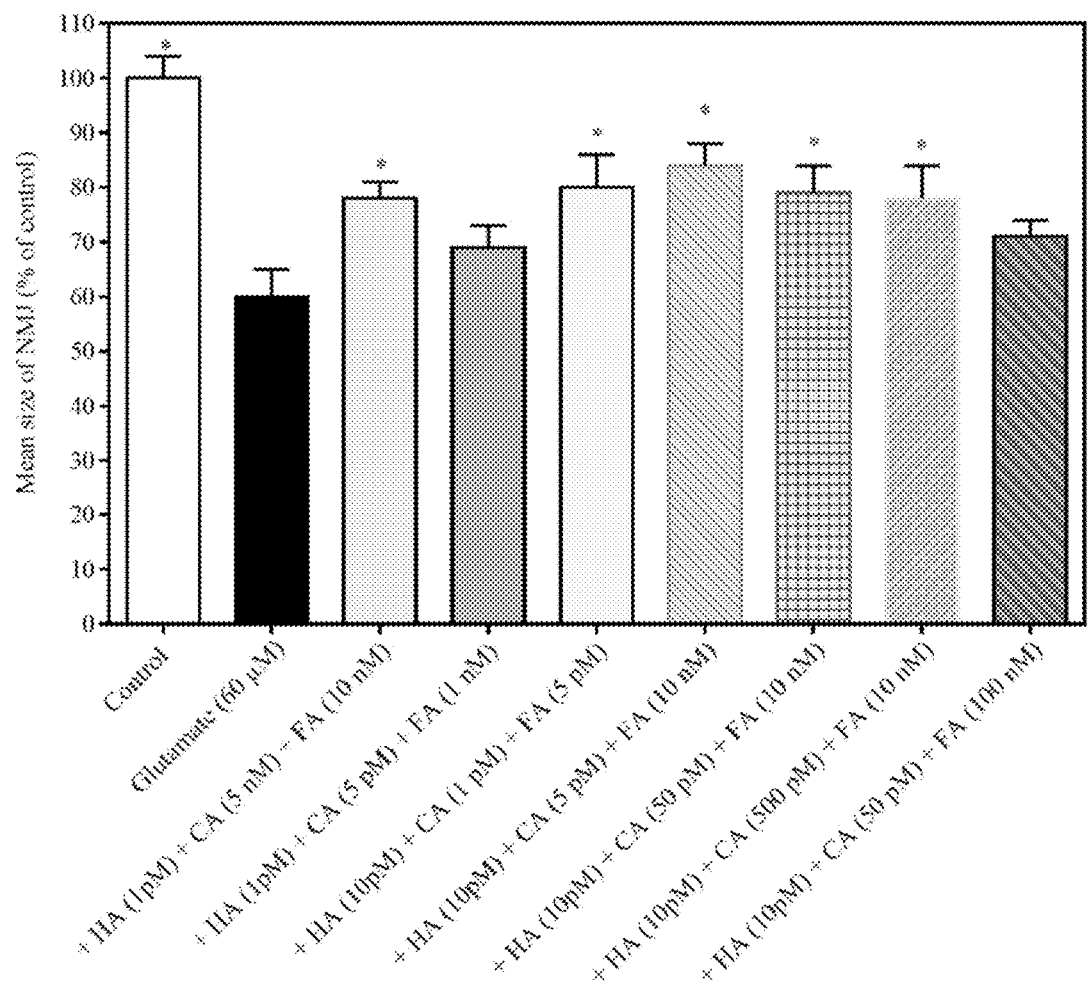

In presence of the mixture of HA/CA/FA a large and significant protective effect was observed for almost all tested mixes (FIG. 9d)

It could be mentioned that the mixture of the 3 compounds was active at all the test concentrations in which separate compounds were not.

FIG. 10 show that glutamate (60 µM-20 min) induced a large and significant decrease of the total neuronal network innervating muscle cells as previously shown in literature [Combes et al., 2015—previously cited].

Figure 10A:
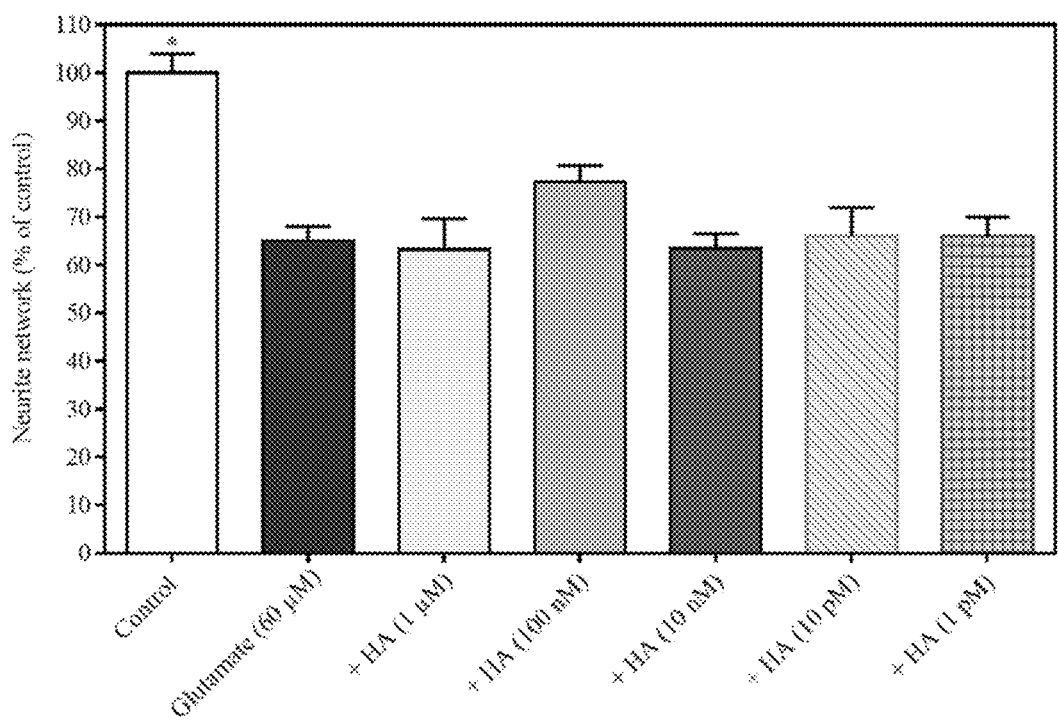
Figure 10B:
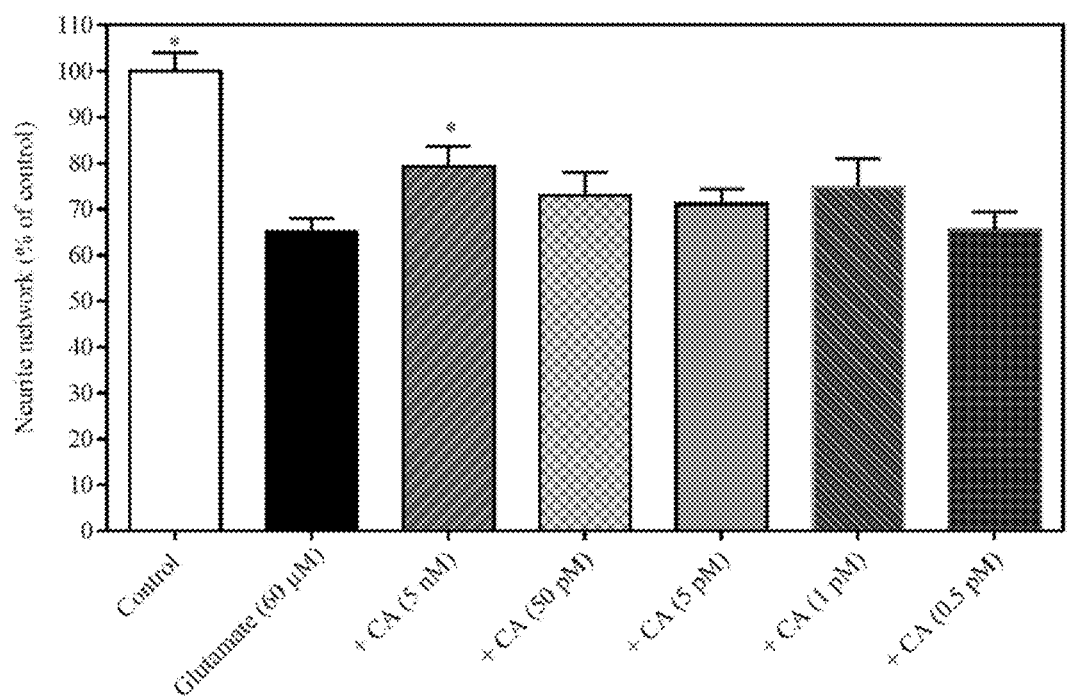
Figure 10C:
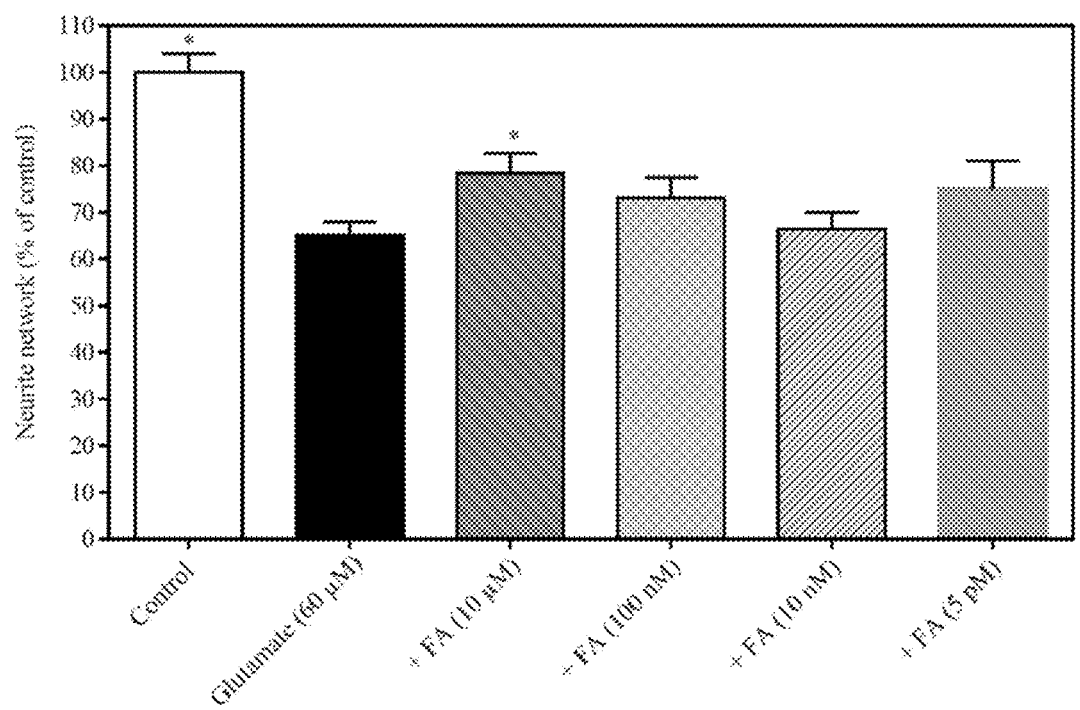

When HA is added (all concentrations tested) no neuronal protective effect has been shown, except a slight neuroprotection which was observed at 100 nM without reaching the significance (FIG. 10a).

When CA is added 1 h before glutamate, it showed a slight protection on neurite network (FIG. 10b), the significance was observed at the highest dose (5 nM). Additionally, FA showed a moderate effect (FIG. 10c) for the highest dose tested (10 µM).

Figure 10D:
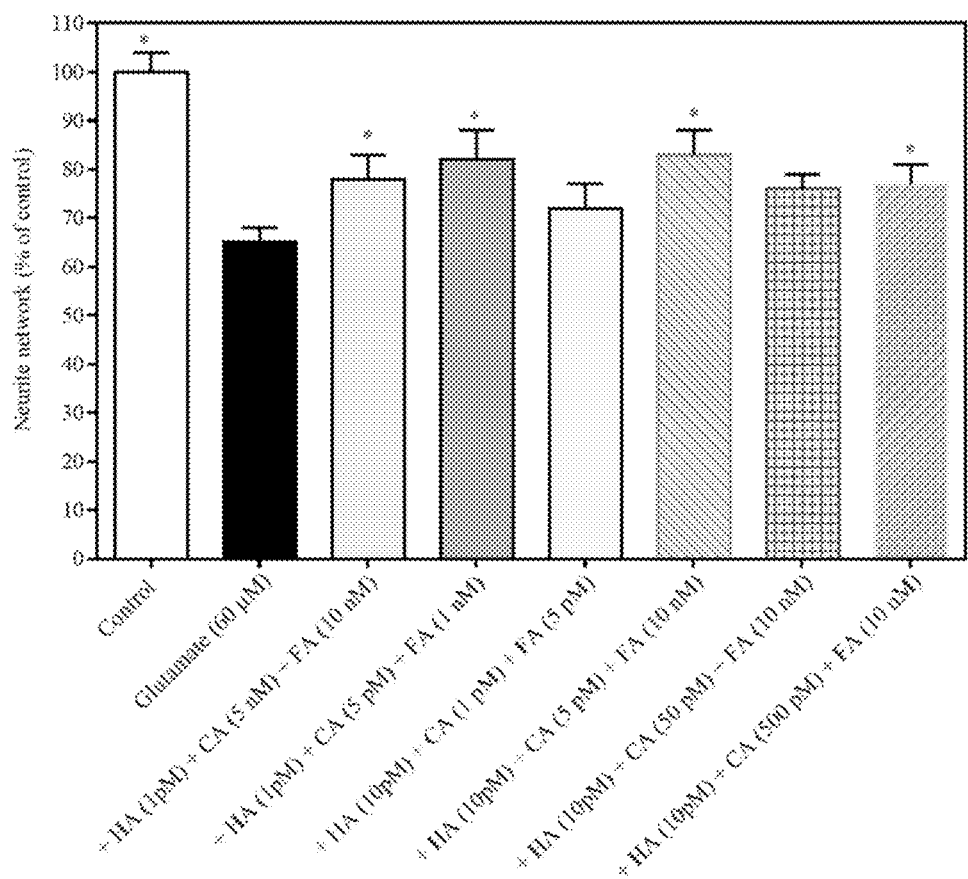

In presence of the mixture of HA/CA/FA a large and significant neuroprotective effect was observed for almost all the tested mixes (FIG. 10d)

These results show that combinations of the 3 molecules (HA/CA/FA) at non active concentrations were able to protect the integrity of NMJs after a glutamate injury. Similar results were observed on the neurite network. For the first time a synergic protective effect of the mixture of these 3 compounds was observed on nerve-muscle co-culture injured by glutamate (a well validated model of ALS).

EXAMPLE 8: PREVENTION OF ACETYLCHOLINESTERASE'S (ACHE) ADVERSE EFFECTS BY HUPERZINE A, CAFFEIC ACID, AND/OR FERULIC ACID

The effect of these 3 single molecules Huperzine A (HA), Caffeic Acid (CA) and Ferulic Acid (FA) was assessed on cortical neurons injured with glutamate a well validated in vitro model of Alzheimer's Disease (Meraz-Ríos et al. (2014) Oxid Med Cell Longev. 2014: 375968).

In light of these results, the effect of the mix of the 3 compounds on AchE activity was assessed. HA is widely proved to be a potent, selective inhibitor of AChE [reviewed by Wang et al. (2006), Acta Pharmacol Sin.; 27(1):1-26]. As a specific AChE Inhibitor (AChEI), the adverse effects of HA are related to the well-known cholinergic activity.

The aim of this study was to see if this specific AchEI activity was potentiated by the mixture and then whether the side adverse effect of HA could be potentiated by the mixture.

1. Experimental section a. HA, CA and FA and mixture HA/CA/FA

Test compounds alone or in association in mixture were solved at different concentrations in medium and then pre-incubated with kit of measure AchE (Promega, France).

b. HA, CA and FA and NSP01-001-E001 (Extract of *Huperzia serrata*, Using Mixture of HA/CA/FA)

Test compounds alone or in association in the NSP01-001-E001 prepared according to example 4 were solved at different concentrations in medium and then pre-incubated with kit of measure AchE (Promega, France).

c. AchE Assay

Kit achetylcholinesterase (Abcam ref ab138871) was used. Briefly, 50 µL of each compounds (HA, CA or FA or mixture or extract) was added to 50 µl of standard solution. A 10-minutes incubation time was applied. The absorbance was assessed at 410 nm.

The activity of the AchE was evaluated versus an AchE activity standard curve.

Data were expressed in percentage of control conditions (no compound=100%). All values were expressed as mean+/−SEM (s.e.mean) (n=6 wells per condition per culture). Graphs and statistical analyses on the different conditions (ANOVA followed by PLSD Fisher's test when allowed, were performed using GraphPad Prism software version 5.0).

2. Results

They are shown in FIGS. 11 and 12.

FIG. 11 shows an effect dose curve of HA. The inhibition of the enzyme was observed from 10 pM up to 10 nM. Interestingly, CA and FA was almost inactive (~8% inhibition) at the doses tested (respectively 50 pM and 100 pM).

The mixture of the 3 compounds did not show any better or lower efficacy in the inhibition of the enzyme. The effect was similar to the one observed with the same dose of HA used as single compound. At the highest dose of the mixture of the 3 compounds (HA 100 pM), the inhibitory effect was similar to the inhibition of HA used alone.

FIG. 12 shows an effect dose curve of HA. The inhibition of the enzyme was observed from 10 pM up to 10 nM.

NSP01-001-E001 prepared according to example 4 was tested on the AchE activity. The doses of the extract contained the corresponding doses of HA tested alone.

Interestingly, similar effect dose curves were observed between NSP01-001-E001, the mixture of the 3 compounds and HA (equivalent doses), no increase nor decrease of the inhibitory effect of the AchE enzyme was observed.

No potentiation of synergistic effect was observed for the NSP01-001-E001 (containing HA but also CA and FA).

All these results show that an original extract (NSP01-001-E001) allows for the first time the safe use of HA. This extract shows the neuroprotective and neuro-restorative activities of HA in a safe range of concentration (i.e in which the adverse events were abolished).

The invention claimed is:

1. A method for retarding the progression of or treating a neurodegenerative disease or condition in a subject, comprising administering to the subject an effective amount of a combination composition comprising as active components, in synergistically effective amounts:
   (i) a huperzine comprising at least one huperzine A of natural or synthetic origin, a pharmaceutically acceptable salt thereof, or a plant extract containing huperzine A;
   (ii) hydroxycinnamic acids comprising
      caffeic acid of natural or synthetic origin, or a plant extract containing caffeic acid, and
      ferulic acid of natural or synthetic origin, or a plant extract containing ferulic acid;
   wherein the molar ratio of huperzine/caffeic acid/ferulic acid is between from 0.01/0.5/10 to 0.1/5/1000.

2. The method according to claim 1, wherein said neurodegenerative disease or condition is selected from the group consisting of: Alzheimer's disease (AD), senile dementia of AD type (SDAT), Parkinson's disease, Lewis body dementia, vascular dementia, autism, myasthenia gravis, Lambert Eaton disease, mild cognitive impairment (MCI), age-associated memory impairment (AAMI), neuronal problems associated with ageing, and (i) non-cognitive neurodegeneration, (ii) non-cognitive neuromuscular degeneration, (iii) motor-sensory neurodegeneration, or (iv) receptor dysfunction or loss in the absence of cognitive, neural and neuromuscular impairment, in a human or non-human animal subject suffering from, or susceptible to, any of Parkinson's disease, postencephalitic Parkinsonism, depression, schizophrenia, muscular dystrophy, Fuch's dystrophy, corneal dystrophy, reflex sympathetic dystrophy syndrome (RSDS), neurovascular dystrophy, Huntington's disease, motor neurone diseases, amyotrophic lateral sclerosis (ALS), multiple sclerosis, postural hypotension, traumatic neurodegeneration, Batten's disease, Cockayne syndrome, Down syndrome, corticobasal ganglionic degeneration, multiple system atrophy, cerebral atrophy, olivopontocerebellar atrophy, dentatorubral atrophy, pallidoluysian atrophy, spinobulbar atrophy, optic neuritis, subacute sclerosing panencephalitis (SSPE), attention deficit disorder, post-viral encephalitis, post-poliomyelitis syndrome, Fahr's syndrome, Joubert syndrome, Guillain-Barre syndrome, lissencephaly, Moyamoya disease, neuronal migration disorders, autistic syndrome, polyglutamine disease, Niemann-Pick disease, progressive multifocal leukoencephalopathy, pseudotumor cerebri, Refsum disease, Zellweger syndrome, supranuclear palsy, Friedreich's ataxia, spinocerebellar ataxia type 2, Rhett syndrome, Shy-Drager syndrome, tuberous sclerosis, Pick's disease, chronic fatigue syndrome, neuropathies, prion-based neurodegeneration, Joseph's disease, acute disseminated encephalomyelitis, arachnoiditis, vascular lesions of the central nervous system, loss of extremity neuronal function, or Charcot-Marie-Tooth disease.

3. A method for retarding the progression of or treating a neurodegenerative disease or condition in a subject, comprising administering to the subject an effective amount of a combination composition comprising as active components, in synergistically effective amounts:
   (i) a huperzine comprising at least one huperzine A of natural or synthetic origin, a pharmaceutically acceptable salt thereof, or a plant extract containing huperzine A;
   (ii) hydroxycinnamic acids consisting of
      caffeic acid of natural or synthetic origin, or a plant extract containing caffeic acid, and
      ferulic acid of natural or synthetic origin, or a plant extract containing ferulic acid.

4. A method for retarding the progression of or treating a neurodegenerative disease or condition in a subject, comprising administering to the subject an oral, transdermal, topical, or parenteral dosage form comprising an effective amount of a combination composition comprising as active components, in synergistically effective amounts:
   (i) a huperzine comprising at least one huperzine A of natural or synthetic origin, a pharmaceutically acceptable salt thereof, or a plant extract containing huperzine A;
   (ii) hydroxycinnamic acids comprising
      caffeic acid of natural or synthetic origin, or a plant extract containing caffeic acid, and
      ferulic acid of natural or synthetic origin, or a plant extract containing ferulic acid, and the combination composition further comprising a pharmaceutically acceptable excipient.

5. The method according to claim 1 wherein the molar ratio huperzine/caffeic acid/ferulic acid is between from 0.01/0.5/10 to 0.1/0.5/1000.

6. The method according to claim 1 wherein the molar ratio huperzine/caffeic acid/ferulic acid is equal to 0.01/50/100.

7. The method according to claim 1 wherein the molar ratio huperzine/caffeic acid/ferulic acid is equal to 0.01/5/100.

8. The method according to claim 1 wherein the hydroxycinnamic acids further comprise one or more acids selected from the group consisting of α-cyano-4-hydroxycinnamic acid, cichoric acid, cinnamic acid, chlorogenic acid, diferulic acids, coumaric acid, coumarin, and sinapinic acid.

9. The method according to claim 1, wherein an additional huperzine is selected from the group consisting of huperzine B, analogs thereof, and mixtures thereof.

10. The method according to claim 1, wherein the molar ratio huperzine/caffeic acid/ferulic acid is 0.01/0.5/100 or 0.01/5/100.

11. The method according to claim 2, wherein the muscular dystrophy is one of facioscapulohumeral muscular dystrophy (FSH), Duchenne muscular dystrophy, Becker muscular dystrophy, Bruce's muscular dystrophy, or myotonic dystrophy.

12. The method according to claim 2, wherein the neuropathy is one of hereditary neuropathy, diabetic neuropathy, or anti-mitotic neuropathy.

13. The method according to claim 2, wherein the prion-based neurodegeneration is one of Creutzfeldt-Jakob disease (CJD), variant CJD, new variant CJD, bovine spongiform encephalopathy (BSE), Gerstmann-Straussler-Scheinker disease (GSS), Fatal familial insomnia (FFI), kuru, or Alper's syndrome.

14. The method according to claim 4, wherein an additional huperzine is selected from the group consisting of huperzine B, analogs thereof, and mixtures thereof.

* * * * *